US008293530B2

(12) United States Patent
Burgess et al.

(10) Patent No.: US 8,293,530 B2
(45) Date of Patent: Oct. 23, 2012

(54) METHOD AND APPARATUS FOR MANUFACTURING PLASMA BASED PLASTICS AND BIOPLASTICS PRODUCED THEREFROM

(75) Inventors: James E. Burgess, Gibsonia, PA (US); Phil G. Campbell, Pittsburgh, PA (US); Lee E. Weiss, Pittsburgh, PA (US); Jason Smith, Pittsburgh, PA (US)

(73) Assignees: Carnegie Mellon University, Pittsburgh, PA (US); Allegheny-Singer Research Institute, Pittsburgh, PA (US)

( * ) Notice: Subject to any disclaimer, the term of this patent is extended or adjusted under 35 U.S.C. 154(b) by 792 days.

(21) Appl. No.: 11/873,751

(22) Filed: Oct. 17, 2007

(65) Prior Publication Data

US 2008/0111272 A1    May 15, 2008

Related U.S. Application Data

(60) Provisional application No. 60/852,368, filed on Oct. 17, 2006, provisional application No. 60/961,580, filed on Jul. 23, 2007.

(51) Int. Cl.
*C12N 5/078* (2010.01)
(52) U.S. Cl. ............................................. 435/372; 435/2
(58) Field of Classification Search ................ 435/2, 372
See application file for complete search history.

(56) References Cited

U.S. PATENT DOCUMENTS

| | | | |
|---|---|---|---|
| 1,786,488 A | 12/1930 | Hombert | |
| 2,385,802 A | 10/1945 | Ferry | |
| 2,385,803 A | 10/1945 | Cohn et al. | |
| 2,457,804 A | 1/1949 | Bower | |
| 2,492,458 A | 12/1949 | Bering | |
| 2,533,004 A | 12/1950 | Ferry et al. | |
| 2,576,006 A | 11/1951 | Ferry et al. | |
| 3,523,807 A * | 8/1970 | Gerendas | 106/156.31 |
| 4,067,119 A * | 1/1978 | Overton | 34/384 |
| 4,352,883 A | 10/1982 | Lim | |
| 4,440,921 A | 4/1984 | Allcock et al. | |
| 4,495,174 A | 1/1985 | Allcock et al. | |
| 4,548,736 A | 10/1985 | Muller et al. | |
| 4,820,626 A | 4/1989 | Williams et al. | |
| 4,880,622 A | 11/1989 | Allcock et al. | |
| 5,112,457 A | 5/1992 | Marchant | |
| 5,126,529 A | 6/1992 | Weiss et al. | |
| 5,204,055 A | 4/1993 | Sachs et al. | |
| 5,286,573 A | 2/1994 | Prinz et al. | |
| 5,293,772 A | 3/1994 | Carr, Jr. | |
| 5,301,415 A | 4/1994 | Prinz et al. | |
| 5,301,863 A | 4/1994 | Prinz et al. | |
| 5,476,777 A | 12/1995 | Holly et al. | |
| 5,502,034 A | 3/1996 | Holly et al. | |
| 5,510,077 A | 4/1996 | Dinh et al. | |
| 5,518,680 A | 5/1996 | Cima et al. | |
| 5,523,293 A | 6/1996 | Jane et al. | |
| 5,527,692 A | 6/1996 | Holly et al. | |
| 5,585,007 A | 12/1996 | Antanavich et al. | |
| 5,630,842 A | 5/1997 | Brodniewicz | |
| 5,653,925 A | 8/1997 | Batchelder | |
| 5,700,289 A | 12/1997 | Breitbart et al. | |
| 5,709,854 A | 1/1998 | Griffith Cima et al. | |
| 5,716,413 A | 2/1998 | Walter et al. | |
| 5,841,950 A | 11/1998 | Wang et al. | |
| 5,855,583 A | 1/1999 | Wang et al. | |
| 5,863,297 A | 1/1999 | Walter et al. | |
| 5,878,193 A | 3/1999 | Wang et al. | |
| 5,906,828 A | 5/1999 | Cima et al. | |
| 5,916,524 A | 6/1999 | Tisone | |
| 5,944,754 A | 8/1999 | Vacanti | |
| 6,037,457 A | 3/2000 | Lord | |
| 6,054,122 A | 4/2000 | MacPhee et al. | |
| 6,074,663 A | 6/2000 | Delmotte et al. | |
| 6,083,902 A | 7/2000 | Cederhom-Williams | |
| 6,102,850 A | 8/2000 | Wang et al. | |
| 6,139,574 A | 10/2000 | Vacanti et al. | |
| 6,143,293 A | 11/2000 | Weiss et al. | |
| 6,165,486 A | 12/2000 | Marra et al. | |
| 6,203,573 B1 | 3/2001 | Walter et al. | |
| 6,233,504 B1 | 5/2001 | Das et al. | |
| 6,270,793 B1 | 8/2001 | Van Dyke et al. | |
| 6,322,785 B1 | 11/2001 | Landesberg et al. | |
| 6,325,808 B1 | 12/2001 | Bernard et al. | |
| 6,331,181 B1 | 12/2001 | Tierney et al. | |
| 6,331,578 B1 | 12/2001 | Turner et al. | |
| 6,385,509 B2 | 5/2002 | Das et al. | |
| 6,394,998 B1 | 5/2002 | Wallace et al. | |
| 6,454,811 B1 | 9/2002 | Sherwood et al. | |
| 6,472,162 B1 | 10/2002 | Coelho et al. | |
| 6,485,751 B1 | 11/2002 | Wang | |
| 6,530,958 B1 | 3/2003 | Cima et al. | |
| 6,547,994 B1 | 4/2003 | Monkhouse et al. | |
| 6,548,729 B1 * | 4/2003 | Seelich et al. | 602/48 |
| 6,589,557 B2 * | 7/2003 | Straub et al. | 424/484 |
| 6,692,738 B2 | 2/2004 | MacLaughlin et al. | |
| 6,705,850 B1 | 3/2004 | Fofonoff | |
| 6,730,299 B1 | 5/2004 | Tayot et al. | |
| 6,740,736 B2 | 5/2004 | McCreath | |
| 6,808,659 B2 | 10/2004 | Schulman et al. | |

(Continued)

FOREIGN PATENT DOCUMENTS

DE    10018987 A1    10/2001

(Continued)

OTHER PUBLICATIONS de Man, K et al. Antigenic properties of Bioplast. Int. J. Oral Surg. 1978. 7: 564-568.*

(Continued)

*Primary Examiner* — Allison Ford
*Assistant Examiner* — Susan E Fernandez
(74) *Attorney, Agent, or Firm* — Fish & Richardson P.C.

(57) ABSTRACT

A method of making a bioplastic, and a bioplastic produced thereby, by using human plasma in which human plasma is clotted, either dried through its gel phase or dried and powdered, and processed into a bioplastic with the addition of at least one plasticizer followed by forming and heating to form a final bioplastic construct.

26 Claims, 4 Drawing Sheets

U.S. PATENT DOCUMENTS

| | | | |
|---|---|---|---|
| 6,855,329 | B1 | 2/2005 | Shakesheff et al. |
| 6,921,412 | B1 | 7/2005 | Black et al. |
| 6,979,307 | B2 | 12/2005 | Beretta et al. |
| 6,998,418 | B1 | 2/2006 | Sung et al. |
| 7,056,722 | B1 | 6/2006 | Coelho et al. |
| 7,135,027 | B2 | 11/2006 | Delmotte |
| 7,148,209 | B2 | 12/2006 | Hoemann et al. |
| 8,017,157 | B2 | 9/2011 | Yoo et al. |
| 2001/0005488 | A1 | 6/2001 | Hirao et al. |
| 2001/0051833 | A1 | 12/2001 | Walter et al. |
| 2002/0054901 | A1 | 5/2002 | Gainey et al. |
| 2003/0054330 | A1* | 3/2003 | Fischer et al. ............ 435/2 |
| 2003/0175410 | A1 | 9/2003 | Campbell et al. |
| 2004/0078077 | A1 | 4/2004 | Binette et al. |
| 2004/0124564 | A1* | 7/2004 | Noorjahan et al. ........ 264/488 |
| 2004/0146543 | A1 | 7/2004 | Shimp et al. |
| 2005/0142208 | A1 | 6/2005 | Yoo et al. |
| 2005/0158535 | A1* | 7/2005 | Zhang et al. .......... 428/304.4 |
| 2005/0226904 | A1 | 10/2005 | Choi et al. |
| 2006/0019389 | A1 | 1/2006 | Yayon et al. |
| 2006/0093644 | A1 | 5/2006 | Quelle et al. |
| 2006/0172008 | A1 | 8/2006 | Yayon et al. |
| 2006/0241776 | A1 | 10/2006 | Brown et al. |
| 2007/0036766 | A1 | 2/2007 | Kevy et al. |
| 2007/0037737 | A1 | 2/2007 | Hoemann et al. |
| 2007/0148142 | A1 | 6/2007 | Yoo et al. |
| 2008/0286329 | A1 | 11/2008 | Campbell et al. |
| 2010/0254900 | A1 | 10/2010 | Campbell et al. |
| 2012/0003193 | A1 | 1/2012 | Campbell et al. |
| 2012/0003279 | A1 | 1/2012 | Campbell et al. |
| 2012/0003324 | A1 | 1/2012 | Campbell et al. |

FOREIGN PATENT DOCUMENTS

| | | | |
|---|---|---|---|
| EP | 0701801 | B1 | 3/1996 |
| EP | 1275397 | A3 | 1/2003 |
| FR | 2583334 | A1 | 12/1986 |
| WO | WO8100516 | A1 | 3/1981 |
| WO | WO8603122 | A1 | 6/1986 |
| WO | WO9511007 | A1 | 4/1995 |
| WO | WO9515763 | A1 | 6/1995 |
| WO | WO9622115 | A1 | 7/1996 |
| WO | WO9812274 | A1 | 3/1998 |
| WO | WO9814135 | A1 | 4/1998 |
| WO | WO0178968 | A1 | 10/2001 |
| WO | WO03079985 | A3 | 10/2003 |
| WO | WO03084937 | A3 | 10/2003 |
| WO | WO03094937 | A1 | 11/2003 |
| WO | WO03007873 | A3 | 3/2004 |
| WO | WO2005037108 | A3 | 4/2005 |
| WO | WO/2007/126411 | | 11/2007 |
| WO | WO2007127834 | A3 | 11/2007 |
| WO | WO2009014776 | A1 | 1/2009 |

OTHER PUBLICATIONS

Yao, C et al. Preparation of networks of gelatin and genipin as degradable biomaterials. Materials Chemistry and Physics. 2004. 83: 204-208.*

Draghi, L et al. Microspheres leaching for scaffold porosity control. Journal of Materials Science: Materials in Medicine. 2005. 16: 1093-1097.*

Marx, RE. Platelet-rich plasma (PRP): What is PRP and what is not PRP? Implant Dentistry. 2001. 10(4): 225-228.*

Bailey and Ingraham, "Chemical, clinical, and immunological studies on the products of human plasma fractionation. xxii. fibrin films in neurosurgery, with special reference to their use in the repair of dural defects and in the prevention of meningocerebral adhesions ," *J. Clin. Invest.*, 1944, 23:597-600.

Butler et al, "Current progress in the production of recombinant human fibrinogen in the milk of transgenic animals," *Thromb Haemost.*, 1997, 78:537-542.

Butler et al., "Secretion of Recombinant Human Fibrinogen by the Murine Mammary Gland ," *Transgenic Res.*, 2004, 13:437-450.

Cronkite et al., "Use of thrombin and fibrinogen in skin grafting," *J Am Med Assoc.*, 1944, 124:976-978.

Ferry et al., Chemical, clinical, and immunological studies on the products of human plasma fractionation , J. Clin. Invest., 1944, 23:566-572.

Ferry et al., "Preparation and Properties of Serum and Plasma Proteins. IX. Human Fibrin in the Form of an Elastic Film," *Am. Chem. Soc J.*, 1947, 69:400-409.

Gerendas, "Bioplasts and their use in surgery," *Ther. Hung.*, 1959, 7:8-16.

Gerendas, "Fibrin products as aids in hemostasis and wound healing," *Fibrinogen*, 1968, Laki, K., Ed., Marcel Dekker, New York, Chapter 13, pp. 277-316.

Prunkard et al., "High-level expression of recombinant human fibrinogen in the milk of transgenic mice," *Nat. Biotechnol.*, 1996, 4:867-871.

Zinner et al., "A new method of arthroplasty," *Acta Med. Acad. Sci. Hung.*, 1955, 7:217-222.

Marx, "Platelet-rich plasma (PRP): What is PRP and what is not PRP?" Implant Dentistry, 2001, 10(4):225-228.

Definition of particulate; Sep. 18,2008; 4 pages.

Aeschlimann et al; Cross-linking of laminin-nidogen complexes by tissue transglutaminase. A novel mechanism for basement membrane stabilization; J Biol Chem; 1991; pp. 266:15308-15317.

Aeschlimann et al; Tissue transglutaminase and factor XIII in cartilage and bone remodeling; Semin Throm Hemost; 1996; pp. 22:437-443.

Aeschlimann et al; Transglutaminases: protein cross-linking enzymes in tissues and body fluids; Throm Haemost; 1994; pp. 71:402-415.

Amon et al; Improving manufacturing quality by combining experimental and statistical methods; Proceedings of the 1997 NSF Design and Manufacturing Grantees Conference, Society of Manufacturing Engineers; 1997.

Amon et al; Shape deposition manufacturing with microcasting: processing, thermal and mechanical issues; ASME Journal of Manufacturing Science and Engineering; 1998; pp. 120:656-667.

Amrani et al; Wound healing. Role of commercial fibrin sealants; Ann N Y Acad Sci; 2001; pp. 936:566-579.

Angerer et al; Regulative development of the sea urchin embryo: signaling cascades and morphogen gradients; Semin Cell Dev Biol; 1999; pp. 10:327-334.

Arras et al; the delivery of angiogenic factors to the heart by microsphere therapy; Nat Biotechnol; 1998; pp. 16:159-162.

Aspenberg et al; Dose-dependent stimulation of bone induction by basic fibroblast growth factor in rats; Acta Orthop. Scand.; 1991; pp. 62:481-484.

Baffour et al; Enhanced angiogenesis and growth of collaterals by in vivo administration of recombinant basic fibroblast growth factor in a rabbit model of acute lower limb ischemia: Dose-dependent effect of basic fibroblast growth factor; J. Vasco Surg.; 1992; pp. 16:181-191.

Bale et al; Strain enhancement of elastic modulus in fine fibrin clots; Throm Res; 1988; pp. 52:565-572.

Basilico et al; the FGF family of growth factors and oncogenes; Advance Cancer Res.; 1992; pp. 59:115-165.

Bates et al; Vascular endothelial growth factor and microvascular permeability; Microcir.; 1999; pp. 6:83-96.

Baustista et al; Insulin-like growth factors I and II are present in the skeletal tissue often vertebrates; Metabolism; 1993; pp. 39:96-100.

Bauters et al; Recovery of disturbed endothelium-dependent flow in the collateral-perfused rabbit ischemic hindlimb following administration of vascular endothelial growth factor; Circulation; 1995; pp. 91:2802-2809.

Bedino; Embalming Chemistry: Glutaraldehyde Versus Formaldehyde; Expanding Encyclopedia of Mortuary Practices; 2003; pp. 649:2614-2632.

Bellamkonda et al; Review: Tissue Engineering in the Nervous System; Biotechnology and Bioengineering; 1994; pp. 43:543-544.

Bosch et al; Guided bone regeneration in calvarial bone defects using polytetrafluorethylene membranes; Cleft Palate Craniofac J; 1995; pp. 32:311-317.

Bose et al; Processing of bioceramic implants via fused deposition process; Solid Freeform Fabrication Symposium; 1998.

Bousfield et al; Nonlinear analysis of the surface tension driven breakup of viscoelastic filaments; J. Non-Newtonian Fluid Mech.; 1986; pp. 21:79-97.

Britland et al; Micropatterning Proteins and Synthetic Peptides on Solid Supports: A Novel Application for Microelectronics Fabrication Technology; Biotechnology Progress; 1992; pp. 8:155-160.

Brown et al; Fibroblast migration in fibrin gel matrices; Am J Pathol; 1993; pp. 142:273-283.

Burgess et al; Characterization and cDNA Cloning of phospholipase C-?, a major substrate for heparin-binding growth factor I (acidic fibro blast growth facto)-activated tyrosine kinase; Mol. Cell. Biol.; 1990; pp. 10:4770-4777.

Burgess et al; The heparin-binding (fibroblast) growth factor family of proteins; Ann. Rev. Biochem.; 1989; pp. 58:575-606.

Campbell et al; Autologous Plastics(Poster); 2007, 1 page.

Campbell et al; Autologous Plastics(Slides); 2007, 9 pages.

Campbell et al; Biomaterial modification of bone growth enhancement: Covalent bonding of insulin-like growth factor-I to metal surfaces; 81st Endocrine Society Meeting; 1999.

Campbell et al; Insulin-like growth factor (IGF)-bindingprotein-5-(201-218) region regulates hydroxyapatite and IGF-I binding; Am J. Physiol.; 1997; pp. 273:E1005-E1013.

Campbell et al; Insulin-like growth factor binding protein (IGFBP) inhibits binding and biological activity of IGFs on human osteosarcoma cells.; J Cell Physiol; 1991; pp. 149:293-300.

Campbell et al; Insulin-like growth factor-binding protein-3 binds fibrinogen and fibrin; J. Biol. Chem.; 1999; pp. 274:30215-30221.

Carmeliet; Mechanisms of angiogenesis and arteriogenesis; Nature Med; 2000; pp. 6:389-395.

Carr et al; Effect of fibrin structure on plasmin-mediated dissolution of plasma clots; Blood Coagul Fibrinolysis; 1995; pp. 6:567-573.

Chen et al; Gradient micro pattern immobilization of EGF to investigate the effect of artificial juxtacrine stimulation; Biomaterials; 2001; pp. 22:2453-2457.

Chen et al; y-y cross-linking sites in human and bovine fibrin; Biochemistry; 1971; pp. 10:4487-4491.

Christani et al; Surface tension driven jet break up of strain-hardening polymer solutions; Journal of Non-Newtonian Fluid Mechanics; 2001; pp. 100:9-26.

Chu et al; Ceramic SFF by Direct and indirect stereolithography; Materials Research Society Fall Meeting; 1999; pp. 119-123.

Ciano et al; Macrophage migration in fibrin gel matrices; Lab Invest; 1996; pp. 54:62-70.

Cima et al; Computer-derived microstructures by 3D Printing: Bio- and Structural Materials; Solid Freeform Fabrication Symposium; 1994.

Clark; Fibrin and wound healing; Ann N Y Acad Sci; 2001; pp. 936:355-367.

Clark; Fibrin sealant in wound repair: a systematic survey of literature; Expert Opin Investig Drugs; 2000; pp. 9:2371-2392.

Cooper et al; Automated Fabrication of Complex Molded Parts Using Mold SDM; Materials and Design; 1999; pp. 20:83-89.

Cornejo et al; Development of Bioceramic Tissue Scaffolds via FDC; Ceramic Transaction; 2000; pp. 110:183-195.

Crawford et al; Solid Freeform Fabrication: A New Manufacturing Paradigm; IEEE Spectrum; 1999; pp. 36:34-43.

Dallas; Measuring interactions between ECM and TGF beta-like proteins; Methods Mol. Biol.; 2000; pp. 139:231-243.

Djabourov et al; Structure and Rheology of Gelatin and Collagen Gels; Biorheology; 1993; pp. 30:191-205.

Drew et al; Wound-healing defects in mice lacking fibrinogen; Blood; 2001; pp. 97:3691-3698.

Dubey et al; Neuronal contact guidance in magnetically aligned fibrin gels: effect of variation in gel mechanostructural properties; Biomaterials; 2001; pp. 22:1065-1075.

Dunstan et al; Systemic administration of acidic fibroblast growth factor (FGF-I) prevents bone loss and increases new bone formation in ovariectomized rats; J Bone Min. Res.; 1999; pp. 14:953-959.

Dutta et al; Layered Manufacturing: Current Status and Future Trends; Trans. ASME JCISE; 2001; pp. 1:60-71.

Eiselt et al; Development of technologies aiding large-tissue engineering; Biotechnol Prog; 1998; pp. 14:134-140.

Elcin et al; Extensive in vivo angiogenesis following controlled release of human vascular endothelial cell growth factor: implications for tissue engineering and wound healing; Artif Organs; 2001; pp. 25:558-565.

Elisseeff et al; Controlled-release of IGF-I and TGF-beta 1 in a photopolymerizing hydrogel for cartilage tissue engineering; J Orthop Res; 2001; pp. 19:1098-1104.

Entchev et al; Gradient formation of the TGF-beta homolog DPP; Cell; 2000; pp. 103:981-991.

Eppley et al; Angiogenic enhancement in bone graft healing by basic fibroblast growth factor; Clin. Res.; 1998; pp. 36:A851.

Eppley et al; Enhancement of angiogenesis by bFGF in mandibular bone graft healing in the rabbit; J. Oral Maxillofac. Surg.; 1998; pp. 46:391-398.

Eppley et al; Platelet-Rich Plasma: A Review of Biology and Applications in Plastic Surgery; Plast. Reconstr. Surg.; 2006; pp. 118(6):147e-15e.

Evans et al; Current Applications of Fibrin Sealant in Urologic Surgery; Int. braz. J. Urol.; 2006; 14 pages.

Fasching et al; Planning Robotic Trajectories for Thermal Spray Shape Deposition; ASM Journal of Thermal Spray Technology; 1993; 2:45-50.

Ferrara et al; The biology of vascular endothelial growth factor; Endocrine Reviews; 1997; pp. 18:4-25.

Ferry et al; Preparation and properties of serum and plasma protiens. VIII. The conversion of human fibrinogen to fibrin under various condictions; J. of American Chem Society; 1947; pp. 69:388-400.

Fesus et al; Transglutaminase-sensitive glutamine residues of human plasma fibronection revealed by studying its proteolytic fragments; Eur J Biochem; 1986; pp. 154:371-374.

Filiz et al; Micromilling of microbarbs for medical implants; International Journal of Machine Tools & Manufacture; 2008; pp. 48:459-472.

Finkelman et al; Quantitation of growth factors IGF-I, SGF/IGF-II/ and TGF-beta in human dentin; J. Bone Miner. Res.; 1990; pp. 5:717-723.

Finlayson et al; Crosslinking of rabbit fibrin in vivo; Thromb Diath Haemorrh; 1974; pp. 31:435-438.

Folkman; Angiogenesis—retrospect and outlook; Exs; 1992; pp. 61:4-13.

Folkman; Angiogenesis and angiogenesis inhibition: an overview; Exs; 1997; pp. 79:1-8.

Folkman et al; Angiogenesis research: guidelines for translation to clinical application; Thromb Haemost; 2001; pp. 86:23-33.

Folkman; How the field of controlled-release technology began, and its central role in the development of angiogenesis research; Biomaterials; 1990; pp. 11:615-618.

Folkman; Tumor angiogenesis; Advances in Cancer Research; 1974; pp. 19:331-358.

Gelman et al; Rigidity of fibring gels as measured by quasielastic light scattering; Biopolymers; 1980; pp. 19:1259-1270.

Gilbert et al; Production and Characterization of ECM Powder: Implications for Tissue Engineering Applications; Biomaterials; 2005; pp. 26:1431-1435.

Giordano et al; Mechanical properties of dense polylactic acid structures fabricated by three dimensional printing; J Biomater Sci Polym Ed; 1996; pp. 8:63-75.

Gladner et al; Effects of crosslinking on the rigidity and proteolytic susceptibility of human fibrin clots; Throm Res; 1983; pp. 30:273-288.

Goldin et al; Breakup of laminar capillary jet of viscoelastic fluid; J. Fluid Mech.; 1969; pp. 38:689-711.

Gorman et al; Structural features of glutamine substrates for transglutaminases. Specificities of human plasma factor Xi Ila and the guinea pig liver enzyme toward synthetic pepiides; J Biol Chem.; 1981; pp. 256:2712-5.

Gorman et al; Structural features of glutamine substrates for human plasma factor XIIIa (activated blood coagulation factor XIII); J Biol Chem; 1980; pp. 255:419-427.

Gorman et al; Transglutaminase amine substrates for photochemical labeling and cleavable cross-linking of proteins; J Biol Chem; 1980; pp. 255:1175-1180.

Greenberg et al; Transglutaminases: multifunctional crosslinking enzymes that stabilize tissues; Faseb J; 1991; pp. 5:3071-3077.

Griffith et al; In vitro organogenesis of liver tissue; N Y Acad Sci; 1997; pp. 831:382-397.

Gross et al; The extended active site of guinea pig liver transglutaminase; J Biol Chem; 1975; pp. 250:4648-4655.

Gurdon et al; Single cells can sense their position in a morphogen gradient; Development; 1999; pp. 126:5309-17.

Gutowska et al; Injectable gels for tissue engineering; Anat Rec; 2001; pp. 263:342-349.

Hall et al; Molecular properties of fibrin-based matrices for promotion of angiogensis in vitro; Microvasc Res; 2001; pp. 62:315-326.

Hallman et al; a clinical histologic study of bovine hydroxyapatite in combination with autogenous bone and fibrin glue for maxillary sinus floor augmentation Results after 6 to 8 months of healing; Clin Oral Implants Res; 2001; pp. 12:135-143.

Hauschka et al; Growth factor effects in bone; The Osteoblast and Osteocyte; 1990; pp. 103-170.

Hayen et al; Hyaluronan stimulates tumor cell migration by modulating the fibrin fiber architecture; J Cell Sci; 1999; pp. 112 (Pt 13):2241-2251.

Herbert et al; Effects of fibrin micromorphology on neurite growth from dorsal root ganglia cultured in three-dimensional fibrin gels; J Biomed Mater Res; 1998; pp. 40:551-559.

Herbert et al; Effects of fibrinolysis on neurite growth from dorsal root ganglia cultured in two- and three-dimensional fibrin gels; J Comp Neurol; 1996; pp. 365:380-391.

Hettasch et al; Analysis of factor XIII substrate specificity using recombinant human factor XIII and tissue transglutaminase chimeras; J Biol Chem; 1997; pp. 272:25149-25156.

Hollinger et al; Poly(alpha-hydroxy acid) carrier for delivering recombinant human bone morphogenetic protein-2 for bone regeneration; J. Controlled Release; 1996; pp. 39:287-304.

Hollinger et al; Recombinant human bone morphogenetic protein-2 and collagen for bone regeneration; J. Biomed. Mater. Res.; 1998; pp. 43(4):356-364.

Hollister et al; Design and Manufacture of HA Biomaterial Scaffold for Bone Tissue Engineering; Trans. 44th Orthopaedic Research Society; 1998; 1 page.

Hu et al; Angiogenin promotes invasiveness of cultured endothelial cells by stimulation of cell-associated proteolytic activities; Proc Natl Acad Sci USA; 1994; pp. 91:12096-12100.

Huber et al; Consequences of seven novel mutations on the expression and structure of keratinocyte transglutaminase; J Biol Chem; 1997; pp. 272:21018-21026.

Isner et al; Clinical evidence of angiogenesis after arterial gene transfer of ph VEGF165 in patient with ischemic limb; The Lancet; 1996; pp. 348:370-375.

Isner et al; The role of angiogenic cytokines in cardiovascular disease; Clin. Immunol. Immunopathol.; 1996; pp. 80:S82-S91.

Jackson et al; Fibrin sealant: current and potential clinical applications; Blood Coag. Fibrinolysis; 1996; pp. 7:737-746.

Kachurin et al; Direct-Write Construction of Living Tissue; Mat. Res. Symp.; 2002; pp. 698:351-356.

Kaihara et al; Silicon micromachining to tissue engineer branched vascular channels for liver fabrication; Tissue Eng; 2000; pp. 6:105-117.

Katstra et al; Oral dosage forms fabricated by three dimensional printing; J Control Release; 2000; pp. 66:1-9.

Kiernan; Formaldehyde, Formalin, Paraformaldehyde and Glutaraldehyde: What they are and What They Do; Microscopy Today; 2000; pp. 8-12.

Kim et al; Survival and function of hepatocytes on a novel three-dimensional synthetic biodegradable polymer scaffold with an intrinsic network of channels; Ann. Surg; 1998; pp. 228:8-13.

King et al; Development and in vitro characterization of vascular endothelial growth factor (VEGF)-loaded poly(DL-lactic-co-glycolic acid)/poly(ethylene glycol) microspheres using a solid encapsulation/single emulsion/solvent extraction technique; J. Biomed Mater Res.; 1999; pp. 51:383-390.

Klasgsbrun et al; Regulators of angiogenesis; Annual Review Physiology; 1991; pp. 53:217-239.

Krewson et al; Stabilization of nerve growth factor in controlled release polymers and in tissue; J Biomater Sci Polym Ed; 1996; pp. 8:103-117.

Lasa et al; Delivery of demineralized bone powder by fibrin sealant; J. Plast. Reconstr. Surg.; 1995; pp. 96:1409-1417.

Laurencin et al; Poly(lactic acid) and poly(glycolic acid): Orthopedic surgery applications; American Academy of Orthopaedic Surgeons; 1994; pp. 325-340.

Laurencin et al; Poly(lactide-co-glycolide)/hydroxyapatite delivery of BMP-2-producing cells: a regional gene therapy approach to bone regeneration; Biomaterials; 2001; pp. 22:1271-1277.

Laurencin et al; Use of polyphosphazenes for skeletal tissue regeneration; J. Biomats. Res.; 1993; pp. 27:963-973.

Leblanc et al; Kinetic studies of guinea pig liver transglutaminase reveal a general-base-catalyzed deacylation mechanism; Biochemistry; 2001; pp. 40:8335-8342.

Lee et al; Crosslinking of wild-type and mutant alpha 2-antiplasmins to fibrin by activated factor XIII and by a tissue transglutaminase; J Biol Chem; 2000; pp. 275:37382-37389.

Lee et al; Degradable and injectable poly(aldehyde guluronate) hydrogels for bone tissue engineering; J Biomed Mater Res; 2001; pp. 56:228-233.

Lee et al; Healing of large segmental defects in rat femurs is aided by rhBMP-2 in PLGA matrix; J. Biomed. Mater. Res.; 1994; pp. 28:1149-1156.

Lee et al; Selective Laser Sintering of Bioceramic materials of Implants; Solid Freeform abrication Symposium; 1993; 5 pages.

Lee et al; Tissue-engineered growth of bone by marrow cell transplantation using porous calcium metaphosphate matrices; J Biomed Mater Res; 2001; pp. 54:216-223.

Leong et al; Fabrication of porous polymeric matrix drug delivery devices using the selective laser sintering technique; Proc Inst Mech Eng [H]; 2001; pp. 215:191-201.

Leung et al; Vascular endothelial growth factor is secreted angiogenic mitogen; Science; 1989; pp. 246:1306-1309.

Linkhart et al; Growth factors for bone growth and repair: IGF, TGFβ, and BMP; Bone; 1996; pp. 19:1-12.

Liu et al; A Novel Use of Genipin-Fixed Gelatin as Extracellular Matrix for Peripheral Nerve Regeneration; J. of Bio. App.; 2004; pp. 19(1):21-34, Abstract only.

Lockhart et al; Expression monitoring by hybridization to high-density oligonucleotide arrays; Nature Biotechnology; 1996; pp. 14:1675-1680.

Lom et al; A Versatile Technique for Patterning Biomolecules Onto Glass Coverslips; J. Neurosci. Methods; 1993; pp. 50:385-397.

Lorand et al; Activation of the fibrin stabilizing factor of plasma by thrombin; Arch. Biochem. Biophys.; 1964; pp. 105:58-67.

Lorand; Factor XIII: structure, activation, and interactions with fibrinogen and fibrin; Ann NY Acad Sci; 2001; pp. 936:291-311.

Lu et al; TGF-beta I release from biodegradable polyer microparticles: its effects on marrow stromal osteoblast function; J Bone Join Surg Am; 2001; pp. 83-A Suppl 1:S82-S91.

Maes et al; Impaired angiogenesis and endochondral bone formation in mice lacking the vascular endothelial growth factor isoforms VEGF(1 64) and VEGF(188); Mech Dev; 2002; pp. 111:61-73.

Meinel et al; Stabilizing insulin-like growth factor-I in poly(D,L-lactide-co-glycolide) microspheres; J. Control Release; 2001; pp. 70:193-202.

Micanovic et al; Role of histidine 373 is the catalytic activity of coagulation factor XIII; J Biol Chem; 1994; pp. 269:9190-9194.

Mikos et al; Laminated three dimensional biodegradable foams for use in tissue engineering; Biomaterials; 1993; pp. 14:323-330.

Mitkevich et al; Coagulation factor XIIIa undergoes a conformational change evoked by glutamine substrate. Studies on kinetics of inhibition and binding of XIIIa by a cross-reacting antifibrinogen antibody; J Biol Chem; 1998; pp. 273:14387-14391.

Monteiro et al; Butterfly eyespot patterns: evidence for specification by a morphogen diffusion gradient; Acta Biotheor; 2001; pp. 49:77-88.

Mooney et al; Growing new organs; Sci. Am.; 1999; pp. 280:60-65.

Mosesson; The assembly and structure of the fibrin clot; Nouv Ref Fr Hematol; 1992; pp. 34:11-16.

Mosesson et al; The structure and biological features of fibrinogen and fibrin; Ann NY Acad Sci; 2001; pp. 936:11-30.

Mosher et al; Cross-linking of fibronectin to collagen by blood coagulation Factor XIIIa; J Clin Invest; 1979; pp. 64:781-787.

Muller et al; Electron microscopy of fine fibrin clots and fine and coarse fibrin films. Observations of fibers in cross-section and in deformed states; J Mol Biol; 1984; pp. 174:369-384.

Muller et al; Rheological Characterization of the Gel Point—a New Interpretation; Macromolecules; 1991; pp. 24:1321-1326.

Nakamura et al; Stimulation of bone formation by intraosseous application of recombinant basic fibroblast growth factor in normal and ovariectomized rabbits; J. Bone Joint Surg.; 1997; pp. 15:307-313.

Nam et al; A Novel Fabrication Method of Macroporous Biodegradable Polymer Scaffolds Using Gas Foaming Salt as a Porogen Addi; J of Biomed Materials Res.; 2006; 10 pages.

Nehls et al; A novel, microcarrier-based in vitro assay for rapid and reliable quantification of three-dimensional cell migration and angiogenesis; Microvac Res.; 1995; pp. 50:311-322.

Nehls et al; The configuration of fibrin clots determines capillary morphogenesis and endothelial cell migration; Microvasc Res; 1996; pp. 51:347-364.

Neufeld et al; Vascular endothelial growth factor (VEGF) and its receptors; Faseb J.; 1999; pp. 13:9-22.

Newman et al; Viscosity and elasticity during collagen assembly in vitro: Relevance to matrix-driven translocation; Biopolymers; 1997; pp. 41:337-347.

Nowotny et al; Preparation of fibrin clot samples for tensile stress-strain experiments; Biomaterials; 1981; pp. 2:55-56.

Oklu et al; The latent trans forming growth factor beta binding protein (LTBP) family; Biochem. J.; 2000; pp. 352 Pt 3:601-10.

Ong et al; Residual Stress Control Issues for Thermal Deposition of Polymers in SFF Processes; Solid Freeform Fabrication Proceedings; 2000; pp. 209-218.

Onizawa; Purification and characterization of bone proliferation factors from bovine bone matrix; Kokubyo Gakkai Zasshi; 1987; pp. 53:349-364.

Ono et al; Bone-fibrin mixture in spinal surgery; Clinical Orthopaedics and Related Research; 1992; pp. 275:133-139.

Pedersen et al; Mechanical Properties of the Skin: A Comparison Between Two Suction Cup Methods; Skin Research and Technology; 2003; pp. 9:111-115.

Pimbley et al; Satellite Droplet Formation in a Liquid Jet; IBM J. Res. Dev.; 1977; pp. 21:21-30.

Piper et al; High selectivity of human tissue transglutaminase for immunoactive gliadin peptides: implications for celiac sprue; Biochemistry; 2002; pp. 41:386-393; United States.

Pitts et al; Submicron Multiphoton Free-form Fabrication of Proteins and Polymers: Studies of Reaction Efficiencies and Applications in Sustained Release; Macromolecules; 2000; pp. 33:1514-1523; United States.

Podos et al; Morphogen gradients: new insights from DPP; Trends Genet; 1999; pp. 15:396-402; United States.

Prince et al; Osteopontin, a substrate for transglutaminase and factor XIII activity; Biochem Biophys Res Commun; 1991; pp. 177:1205-1210; United States.

Prinz et al; Novel Applications and Implementations of Shape Deposition Manufacturing; Office Naval Research; 1998; pp. 19-26; United States.

Radomsky et al; Potential role of fibroblast growth factor in enhancement of fracture healing; Clin. Orthop. Rel. Res.; 1998; pp. 355:283-293; United States.

Ranieri et al; Spatial Control of Neuronal Cell Attachment and Differentiation on Covalently Patterned Laminin Oligopeptide Substrates; Intl. J Devel. Neurosci.; 1994; pp. 12(8):725-735; Switzerland.

Ribatti et al; Chorioallantoic membrane capillary bed: a useful target for studying angiogenesis and anti-angiogenesis in vivo; Anat Rec; 2001; pp. 264:317-324; Italy.

Ribatti et al; The Chick Embryo Chorioallantoic Membrane as a Model for in vivo Research on Angiogenesis; Int. J. Dev. Biol.; 1996; pp. 40(6):1189-1197; Italy.

Ribatti et al; The chick embryo chorioallantoic membrane as a model for in vivo research on anti-angiogenesis; Curr Pharm. Biotechnol; 2000; pp. 1:73-82; Italy.

Ribatti et al; The Chick Embryo Chorioallantoic Membrane as an in vivo Wound Healing Model; Pathol Res Pract; 1996; pp. 192:1068-1076; Italy.

Richardson et al; Polymeric system for dual growth factor delivery; Nat Biotechnol.; 2001; pp. 19:1029-1034; United States.

Ringeisen et al; Cell-by-Cell Construction of Living Tissue; Mat. Res. Symp. 2002:Materials Research Society; 2002; pp. 698:329-341; United States.

Roberts et al; Factors affecting the migration and growth of endothelial cells from microvessels of bovine retina; Exp Eye Res; 1990; pp. 50:165-172; United Kingdom.

Robinson et al; Catalytic life of activated factor XIII in thrombi. Implications for fibrinolytic resistance and thrombus aging; Circulation; 2000; pp. 102:1151-1157; United States.

Rodan et al; Effects of acidic and basic fibroblast growth factors on osteoblastic cells; Connect. Tissue Res.; 1989; pp. 20:283-238; United States.

Rodan et al; Fibroblast growth factor and platelet derived growth factor; Cytokines and Bone and Metabolism; 1992; pp. 116-140; United States.

Rodan et al; Growth stimulation of rat calvaria osteoblastic cells by acidic fibroblast growth factor; Endocrinol.; 1987; pp. 121:1917-1923; United States.

Rosengart et al; Therapeutic angiogenesis: a comparative study of angiogenic potential of acidic fibroblast growth factor and heparin; J. Vase Surg; 1997; pp. 26:302-312; United States.

Rowe et al; Multimechanism oral dosage forms fabricated by three dimensional printing; J Control Release; 2000; pp. 66:11-17; United States.

Saharinen et al; Latent transforming growth factor-beta binding proteins (LTBPs)—structural extracellular matrix proteins for targeting TGF-beta action; Cytokine Growth Factor Rev.; 1999; pp. 10:99-117; Finland.

Sahni et al; Binding of basic fibroblast growth factor fibrinogen and fibrin; J Biol Chem; 1998; pp. 273:7554-7559; United States.

Sahni et al; Potentiation of endothelial cell proliferation by fibrin(ogen)-bound fibroblast growth factor-2; J Biol Chem; 1999; pp. 274:14936-14941; United States.

Sakai et al; Tissue transglutaminase facilitates the polymerization of insulin-like growth factor-binding protein-I (IGFBP-I) and leads to loss of IGFBP-I's ability to inhibit insulin-like growth factor-I-stimulated protein synthesis; J Biol Chem; 2001; pp. 276:8740-8745; United States.

Sakata et al; Cross-linking of alpha 2-plasmin inhibitor to fibrin by fibrin-stabilizing factor; J Clin Invest; 1980; pp. 65:290-297; United States.

Sakiyama et al; Incorporation of heparin-binding peptides in fibrin gels enhances neurite extension: an example of designer matrices in tissue engineering; Faseb J; 1999; pp. 13:2214-2224; Switzerland.

Sakiyama-Elbert et al; Controlled release of nerve growth factor from a heparin-containing fibrin-based cell ingrowth matrix; J Control Release; 2000; pp. 69:149-168; Switzerland.

Saltzman et al; Intracranial delivery of recombinant nerve growth factor: release kinetics and protein distribution for three delivery systems; Pharm Res; 1999; pp. 16:232-240; United States.

Sane et al; Vitronectin is a substrate for transglutaminases; Biochem Biophys Res Commun; 1988; pp. 157:115-120; United States.

Schense et al; Cross-linking exogenous bifunctional peptides in fibrin gels with factor XIIIa; Bioconjug Chem; 1999; pp. 10:75-81; United States.

Schlag et al; Fibrin sealant in orthopeadic surgery; Clin. Orthop. Rel. Res.; 1988; pp. 227:269-285; Austria.

Schmaltz et al; Investigation of Transport Phenomena in Microeasting Shape Deposition ManuJacturing via Experiments Designed using Optimal Sampling; ASME National Heat Transfer Conference; 1997; pp. 241-250; United States.

Schmitz et al; Characterization of a rat calvarial nonunion defects; Acta. Anat. Anatomica; 1990; pp. 138:185-192; United States.

Schmitz et al; The critical size defect as an experimental model for craniomandibulofacial nonunions; Clin. Orthop. Rel. Res.; 1986; pp. 205:299-308; United States.

Schonherr et al; Extracellular matrix and cytokines: a functional unit; Dev. Immunol.; 2000; pp. 7:89-101; Malaysia.

Schott et al; Growth factors and angiogenesis; Cardiovasc Res; 1993; pp. 27:1155-1161; United States.

Schrier et al; Recombinant human bone morphogenetic protein-2 binding and incorporation in PLGA microsphere delivery systems; Pharm Dev Technol; 1999; pp. 4:611-621; United States.

Schwartz et al; The influence of fibrin sealant on demineralized bone marix-dependent osteoinduction; Clin Orthop Rel Res; 1989; pp. 238:282-287; Austria.

Scott; An assessment of reasonable tortuosity values; Pharm Res; 2001; pp. 18:1797-1800; United States.

Shainoff et al; Immunoelectrophoretic characterizations of the crosslinking of fibrinogen and fibrin by factor XIIIa and tissue transglutaminase. Identification of a rapid mode of hybrid alpha/gamma-chain cross-linking that is promoted by the gamma-chain cross-linking; U. Biol. Chem.; 1991; pp. 266:6429-6437; United States.

Shen et al; Contribution of fibrin stabilization to clot strength. Supplementation of factor XIII-deficient plasma with the purified zymogen; J Clin Invest; 1983; pp. 71:1336-1341; United States.

Shen et al; Effects of calcium ion and covalent crosslinking on formation and elasticity of fibrin cells; Thromb Res; 1975; pp. 6:255:65; United States.

Sierra et al; A method to determine shear adhesive strength of fibrin sealants; J Appl Biomater; 1992; pp. 3:147-151; United States.

Singhvi et al; Engineering Cell Shape and Function; Science; 1994; pp. 264:696-698; United States.

Singhvi et al; Review: Effect of Substratum Morphology on Cell Physiology; Biotechnology and Bioengineering; 1994; pp. 43:764-771; United States.

Sipe et al; Localization of Bone Morphogenetic Proteins (BMPs}-2, -4, and -6 within Megakaryocytes and Platelets; Bone; 2004; pp. 35(6):1316-1322; United States.

Smith et al; Osseous regeneration in preclinical models using bioabsorbable delivery technology for recombinant human bone morphogenetic protein-2 (rhBMP-2); J. Controlled Rel.; 1995; pp. 36:183-195; United States.

Soker et al; Systems for therapeutic angiogenesis in tissue engineering; World J Urol; 2000; pp. 18:10-8; United States.

Sorensen et al; Localization of trans glutaminase-reactive glutamine residues in bovine osteopontin; Biochem J; 1994; pp. 304 (Pt1):13-6; United Kingdom.

Springer et al; VEGF gene delivery to muscle: potential role for vasculogenesis in adults; Mol Cell; 1998; pp. 2:549-558; United States.

Campbell et al., U.S. Appl. No. 13/177,147, "Methods and Apparatus for Manufacturing Plasma Based Plastics and Bioplastics Produced Therefrom," filed Jul. 6, 2011, 67 pages.

Campbell et al., U.S. Appl. No. 13/357,835, "Barbs for Fixation of Biologic Plastics," filed Jan. 25, 2012, 18 pages.

D 256-06a: Standard Test Method for Determining the Izod Pendulum Impact Resistance of Plastics; pp. 1-20; ASTM International; 2007.

D 4508-06: Standard Test Method for Chip Impact Strength of Plastics; pp. 528-533; ASTM International; 2007.

D 5045-99: Standard Test Method for Plane-Strain Fracture Toughness and Strain Energy Release Rate of Plastic Materials; pp. 795-803; ASTM International; 2007.

D 6272-02: Standard Test Method for Flexural Properties of Unreinforced and Reinforced Plastics and Electrical Insulating Materials by Four-Point Bending; pp. 519-526; ASTM International; 2007.

D 790-07: Standard Test Methods for Flexural Properties of Unreinforced and Reinforced Plastics and Electrical Insulating Materials; pp. 1-11; ASTM International; 2007.

D-638-03: Standard Test Method for Tensile Properties of Plastic; pp. 50-63; ASTM International; 2007.

D695-02a: Stanard Test Method for Compressive Properties of Rigid Plastics; pp. 78-85; ASTM International; 2007.

Strigini et al; Formation of morphogen gradients in the *Drosophila* wing; Semin Cell Dev Biol; 1999; pp. 10:335-344; Germany.

Tabata et al; De novo formation of adipose tissue by controlled release of basic fibroblast growth factor; Tissue Eng; 2000; pp. 6:279-289; Japan.

Tabata; Genetics of morphogen gradients; Nat Rev Genet; 2001; pp. 2:620-630; Japan.

Takagi et al; The reaction of the dura to bone morphogenetic protein (BMP) in repair of skull defects; Ann Surg.; 1982; pp. 196:100-109; United States.

Takeshita et al; Gene transfer of naked DNA encoding for 3 isoforms of vascular endothelial growth factor stimulates collateral circulation development in vivo; Lab. Invest.; 1996; pp. 75:487-502; United States.

Takeshita et al; In vivo evidence that vascular endothelial growth factor stimulates collateral formation by inducing arterial cell proliferation in a rabbit ischemic hindlimb; J Am. Coli. Cardia; 1994; pp. 23:294A; United States.

Takeshita et al; Intramuscular administration of vascular endothelial growth factor induces dose-dependent collateral artery augmentation in a rabbit model of chronic limb ischemia; Circulation; 1994; pp. 90:228-234; United States.

Takeshita et al; Microangiographic assessment of collateral vessel formation following direct gene transfer of vascular endothelial growth factor in rats; Cardiovasc. Res.; 1997; pp. 35:547-552; Japan.

Takeshita et al; Therapeutic angiogenesis: A single intra-arterial bolus of vascular endothelial growth factor augments collateral vessel formation in a rabbit ischemic hindlimb model; J. Clin. Invest.; 1994; pp. 93:662-670; United States.

Teleman et al; Dpp gradient formation in the *Drosophila* wing imaginal disc; Cell; 2000; pp. 103:971-980; Germany.

Toma et al; Autologous fibrin glue in the repair of dural defects in craniofacial resections; J Laryngol Otol; 1992; pp. 106:356-357; United Kingdom.

Valentini et al; Patterned Neuronal Attachment and Outgrowth on Suiface Modified, Electrically Charged Fluoropolymer Substrates; J. Biomaterials Science Polymer Edition; 1933; pp. 5(112):13-36; Netherlands.

Van Hinsbergh et al; Role of fibrin matrix in angiogenesis; Ann NY Acad Sci; 2001; pp. 936:426-437; Netherlands.

Wang et al; Basic fibroblast growth factor enhances bone-graft incorporation: Dose and time dependence in rats; J. Orthop. Res.; 1996; pp. 34:316-323; Sweden.

Wang; Basic fibroblast growth factor for stimulation of bone formation in osteoinductive or conductive implants; Acta. Orthop. Scand. Suppl.; 1996; pp. 269:1-33; United States.

Wang et al; Basic fibroblast growth factor infused at different times during bone graft incorporation. Titanium chamber study in rats; Acta. Orthop. Scand.; 1996; pp. 67:229-236; Sweden.

Wang et al; Basic fibroblast growth factor promotes ingrowth in porous hydroxyapatite; Clin. Orthop. Rel. Res.; 1996; pp. 333:252-260; Sweden.

Wang; Characterization of matrix-induced osteogenesis in rat calvarial bone defects: II. Origins of bone-forming cells; Calcif Tissue Int; 1999; pp. 65:486-493; United States.

Weiss et al; A Rapid Tool Manufacturing System Based on Stereolithography and Thermal Spraying; ASME Manufacturing Review; 1990; pp. 40-48; United States.

Weiss; Process Overview Analytical Chapters; NSF sponsored JTEC/WTEC panel report on rapid prototyping in Europe and Japan; 1997; pp. 5-20; United States.

Weiss et al; Shape Deposition Manufacturing of Heterogeneous Structure; SME Journal of Manufacturing Systems; 1997; pp. 16:239-248; United States.

Weiss; Tissue Engineering: Solid Freeform Fabrication of Scaffolds; Science & Medicine; 2002; pp. 8:6-7; United States.

Wilting et al; Effects of vascular endothelial growth factor and basic fibroblast growth factor: application with corneal grafts on the chorioallantoic membrane; Acta Anat (Basel); 1993; pp. 147:207-215; Germany.

Winter et al; Analysis of Linear Viscoelasticity of a Cross-Linking Polymer at the Gel Point; Journal of Rheology; 1986; pp. 30:367-382; United States.

Wolpert; Positional information and the spatial pattern of cellular differentiation; Journal of Theoretical Biology; 1969; pp. 25:1-47; United Kingdom.

Wong et al; Fibrin-based Biomaterials to Deliver Human Growth Factors; Thromb. Haemost; 2003; pp. 89:573-582; United States.

Wu et al; cidic and basic FGFs dilate arterioles of skeletal muscle through NO-dependent mechanism; Am. J. Physiol.; 1996; pp. 3:1087-1093; United States.

Yancopoulos et al; Vascular-specific growth factors and blood vessel formation; Nature; 2000; pp. 407:242-248; United States.

Yao et al; Biocompatibilty and biodegradation of a bone composite containing tricalcium phosphate and genipin crosslinked gelatin; Journal of Biomedical Material Research; 2004; pp. 69A:709-717; Taiwan.

Yarin; Free Liquid Jets and Films: Hydrodynamics and Rheology; Longman Sci. & Tech; 1993; United States.

Ye et al; Fibrin gel as a three dimensional matrix in cardiovascular tissue engineering; Eur J Cardiothorac Surg.; 2000; pp. 17:587-591; Swaziland.

Zein et al; Processing of 3D scaffolds by fused deposition modeling; International Workshop on Advances in Materials Science and Technology; 2000; Singapore.

Zisch et al; Covalently conjugated VEGF-fibrin matrices for endothelialization; J. Control Release; 2001; pp. 72:101-113; Switzerland.

* cited by examiner

Micromolded Spike Arrays: PBP particle size ≤ 38 μm
Micromolded Spike Arrays: PBP particle size ≤ 150 μm

FIG. 4

METHOD AND APPARATUS FOR MANUFACTURING PLASMA BASED PLASTICS AND BIOPLASTICS PRODUCED THEREFROM

CROSS REFERENCE TO RELATED APPLICATIONS

This application is based on U.S. Provisional Patent Applications No. 60/852,368, filed Oct. 17, 2006, and No. 60/961,580, filed Jul. 23, 2007, on which priority of this patent application is based, and which are hereby incorporated by reference in their entireties.

BACKGROUND OF THE INVENTION

1. Field of the Invention

The invention pertains to bioplastics for patient implantation or application, made at least in part from patient tissue or fluids such as plasma.

2. Description of Related Art

Fibrin-based plastics were invented in the 1940s as part of a U.S. Defense-sponsored research program to develop medical strategies for wounded military personnel. For example, fibrin-based plastics were developed out of the human blood program led by Edwin Cohn at Harvard University. John Ferry, then at Woods Hole, led the group that was involved in developing fibrin elastomers. As a result of this work, elastomeric sheet forms of fibrin were developed and used successfully in neurosurgical applications, burn treatments, and peripheral nerve regeneration. See, for example, Ferry, J.D. et al., *Clin. Invest.* 23:566-572 (1944); Bailey, O.T. et al, *J. Clin. Invest.* 23:597-600 (1944); Cronkite et al., *JAMA*, 124:976-8 (1944); and Ferry J.D. et al., *Am. Chem. Soc J.* 69:400-409 (1947). Hard fibrin plastics were fabricated into implants and were finding clinical success as early as the 1940s. See, for example, U.S. Pat. No. 1,786,488, No. 2,385,802, No. 2,385,803, No. 2,492,458, No. 2,533,004, No. 2,576,006, No. 3,523,807, No. 4,548,736, and No. 6,074,663, all incorporated herein by reference. Research sponsored by the Hungarian government led to the development of similar products in the 1950s through the early 1970s. Forms of hard plastic fibrin was demonstrated to have clinical efficacy in orthopedic applications of bone resurfacing. See, for example, Zinner, N. et al., *Acta Med. Acad. Sci. Hung.*, 7:217-222 (1955); Gerendas, M., *Ther. Hung.*, 7:8-16 (1959); and Gerendas, M., Chapter 13 in *Fibrinogen*, Laki, K., Ed., Marcel Dekker, New York, pp. 277-316 (1968).

Despite the efficacy of fibrin products, concerns about disease transmission from purified human fibrinogen from pooled plasma remained. However, during the late 1970s and thereafter, fibrin was developed as a tissue glue and sealant, and although this application required purified human fibrinogen, new techniques had been developed to ensure the safety of blood products. Consequently, fibrin-based glues and sealants have been used in clinical practice for over twenty years in Europe (and since 1998 in the United States) with no disease transmission concerns. Recently, the development of recombinant human fibrinogen and thrombin and purified salmon fibrinogen and thrombin have helped further to address concerns over both safety and market availability. See, for example, Butler S.P. et al., *Transgenic Res.* 13:437-450 (2004); Prunkard D. et al., *Nat. Biotechnol.* 4:867-871 (1996); Butler S. P. et al, "*Thromb Haemost.* 78:537-542 (1997); U.S. Pat. Nos. 5,527,692; 5,502,034; 5,476,777; 6,037,457; 6,083,902; and U.S. Pat. No. 6,740,736. Autologous sealants and glues are also available (see for example U.S. Pat. No. 6,979,307).

Despite such advances in the field, interest in the use of protein bioplastics in plastic forms, such as fibrin elastomers, has significantly declined over time. Silicone rubber sheets, which were introduced in the 1960s and 1970s, have replaced fibrin elastomeric sheets in the clinic, despite inherent problems with their permanence. There are also limitations with current synthetic bioresorbable plastics, such as polyurethane, polylactic acid (PLA), polylactic-co-glycolic acid (PLGA), polyglycolic acid (PGA) and polycaprolactone. These polymers degrade in the body by hydrolysis, via bulk degradation, or through surface erosion, all of which operate independently of the surrounding biological environment. The inability of these polymers to degrade in response to cellular invasion and to promote directly the ingrowth of host tissues remains a profound limitation of bioresorbable implants.

In contrast, protein bioplastics can degrade in response to cellular proteolytic processes so that degradation occurs in concert with the growth and healing of host tissues. Also, many synthetic materials do not inherently bind growth factors of interest for therapeutic delivery options, whereas fibrin binds to growth factors directly and indirectly through molecular interactions with growth factors, including those with heparin binding domains. However, fibrin materials—including certain of the present inventors' own fibrin-based plastics based on purified fibrinogen/thrombin from pooled human or animal plasma—have certain constraints or limitations such as not inherently containing endogenous growth factors. Moreover, fibrin materials of the prior art are very expensive especially when prepared from human sources and with the required large amounts of starting material necessary to give desired yields. Commonly used synthetic materials, such as bioresorbable polymers, can be associated with inflammatory interactions, whereas these interactions would be less pronounced if one were to use protein-based plastics. Purified fish- or bovine-derived fibrinogen is potentially less expensive—although similar to its purified human counterpart in not containing human growth factors-yet disease transmission and immuno-sensitization with repeated use are potential major drawbacks due to its xenogenic source. Analogously to plastic implants, allogenic bone grafts also have several limitations, including high variability of graft quality from donor to donor. This variability arises from several factors including amount of active endogenous growth factors in each donated graft, and there are no practical means for quality assessment and/or quality control of allogenic bone graft materials with respect to these growth factors.

To date, methods and compositions previously developed for bioplastics, including but not limited to fibrin, elastin and etc., are not sufficiently adaptable for modern clinical use. For example, the original manufacturing methods developed for certain protein-based bioplastics required high temperatures (i.e., as high as 155° C.). Such high temperature processing precludes the use of exogenously added drugs and proteins as well as destroys any inherent biological activity. In addition, methods for making these materials porous have not been reported or developed previously. Prior to the present invention, no one had solved the problem of manufacturing bioplastics while avoiding the disadvantages of known processing techniques, such as high temperatures and pressures and/or difficulty in retaining desirable physical characteristics of the plastics. More importantly of all, perhaps, no one has heretofore addressed how effectively to reduce or eliminate the issues of disease transmission and immune response of bioplastics derived from animal or human pooled donor sources.

Therefore, certain needs remained prior to the present invention. Methods of incorporating heat-sensitive materials such as biological response modifiers, including but not limited to growth factors and extracellular matrix molecules, and drugs into elastomeric and/or pliant and/or hard materials were needed. Compositions having the ability to respond to the local cellular milieu were also needed, with or without spatial patterns in the overall construct or sheet to provided such responses where desired. Prior efforts to crosslink fibrin-based bioplastics were either post-fabrication methods, which generally created unwanted effects such as swelling, or used toxic crosslinking agents such as formaldehyde in addition to representing laborious processes. Fabrication methods were also needed that could be used to control properties of manufactured articles including for example the density, porosity, and mechanical properties of bioplastic materials. Methods of manufacturing biocompatible materials with anisotropic properties were needed, especially with regard to extrusion or directed strain and/or printing technologies to impart such anisotropic properties. For these and other reasons, more reliable, cost-effective substitute tissue graft materials including bioplastics have previously remained an illusive yet important clinical goal.

SUMMARY OF THE INVENTION

In order to meet these and other goals, the present invention is a method of making bioplastics using human plasma either in its whole form or from which one or more constituents have been removed, in which human plasma is clotted either before or after any removal of any desired constituents, dried through its gel phase or dried and powdered, and processed into a bioplastic with an added plasticizer. When elastic or elastomeric sheet materials are made containing the clotted and dried plasma of the present invention, the plasma or plasma fraction is "dried through the gel phase," that is, dried until the plasma or plasma fraction(s) is/are drier than a colloidal plasma gel, and then further processed with a plasticizer (water and/or glycerol) into an elastic or elastomeric plastic in that form. (Because glycerol, glycerin and glycerine are equivalent, hereinafter the word "glycerol" will be used to indicate any or all of glycerol, glycerin and glycerine.) For rubbery-to-hard bioplastics which have little elasticity, quantities of powdered clotted plasma (whole or otherwise) are used to make a bioplastic, again together with a water and/or glycerol plasticizer or other biocompatible plasticizers known in the art. The clotted and dried plasma may alternatively be added to virtually any plastic base material that will cure at the desired temperatures, but generally speaking the clotted and dried plasma plus plasticizer (water and/or glycerol) is used to make a bioplastic material without other structural-plastic-making additives. In other words, except for constituting materials such as powders, additives, biologics or drugs or etc. which do not contribute significantly to the bioplastic itself, the present inventive materials are made predominantly of clotted and dried plasma plus plasticizer. When powdered clotted plasma is used as an ingredient in bioplastics, the powder is generally adjusted to a water content of 5-15% by weight, preferably 8-12% by weight, more preferably 8-10% by weight, prior to mixing the dough. Dough is defined as the combination of plasma powder, plasticizer and any other components that are mixed prior to plastification processing. By contrast, when the plasma or plasma fraction is dried through the gel phase, the water that is inherent from the original plasma clot represents about 10-25% by weight of the starting material. Also, at any time a stabilizer(s) may be added to the plasma constituents to protect during dehydration and rehydration. These stabilizers may include without limitation glycogen, sorbitol, mannitol, trehalose, maltitol, xylitol, isomaltitol, erythritol, amylase, amylopectin, inositol hexasulphate, sulphated beta-cyclodextran, etc. or combinations thereof. In fact, the stabilizer may be any known nontoxic polysaccharide according to the general formula of $C_n(H_2O)_{n-1}$ where n is between 200 and 2500. For those bioplastics in which significant retention of biological activity of constituents is desired, the plasticizing temperature is between 55-65° C. If retention of biological activity is not necessary the clotted dried plasma containing composition may be plasticized at temperatures up to about 150° C., particularly to create harder and/or denser bioplastic materials. In any case, the clotted dried plasma containing admixtures of the present invention are plasticized at 9-25 kpsi (kilopounds per square inch), preferably at 9-15 kpsi and more preferably at least 10.7 kpsi or higher. The resulting plasma-based plastics (PBPs) of the present invention can thus be made with a range of biomechanical and degradation properties. PBPs can be used in a variety of clinical applications, including their use as substitute graft materials, drug delivery carriers, anti-adhesion and barrier membranes, and scaffolds for tissue engineering. PBPs can also be used in cell culture as a non-animal source of endogenous or exogenous growth media.

DESCRIPTION OF THE PREFERRED EMBODIMENT(S)

The present invention is a method of making bioplastics using human plasma either in its whole form or from which one or more constituents have been removed, in which human plasma is clotted either before or after any removal of any desired constituents, dried through its gel phase or dried and powdered, and processed into a bioplastic with an added plasticizer. When elastic or elastomeric sheet materials are made containing the clotted and dried plasma of the present invention, the plasma or plasma fraction is "dried through the gel phase," that is, dried until the plasma or plasma fraction(s) is/are drier than a colloidal plasma gel, and then further processed with a plasticizer (water and/or glycerol) into an elastic or elastomeric plastic in that form. In fact, during the manufacture of elastomeric sheet materials in this way, one or more plasticizers and any crosslinking agents may be contacted onto or admixed into the plasma at any stage of the process. (Because glycerol, glycerin and glycerine are equivalent, hereinafter the word "glycerol" will be used to indicate any or all of glycerol, glycerin and glycerine.) For rubbery-to-hard bioplastics which have little elasticity, quantities of powdered clotted plasma (whole or otherwise) are used to make a bioplastic, again together with a water and/or glycerol plasticizer. The clotted and dried plasma may alternatively be added to virtually any plastic base material that will cure at the desired temperatures, but generally speaking the clotted and dried plasma plus plasticizer (water and/or glycerol) is used to make a bioplastic material without other structural-plastic-making additives. In other words, except for constituting materials such as powders, additives, biologics or drugs or etc. which do not contribute significantly to the bioplastic itself, the present inventive materials are made predominantly of clotted and dried plasma plus plasticizer. When powdered clotted plasma is used as an ingredient in bioplastics, the powder is generally adjusted to a water content of 5-15% by weight, preferably 8-12% by weight, more preferably 8-10% by weight, prior to mixing the dough. By contrast, when the plasma or plasma fraction is dried through the gel phase, the water that is inherent from the original plasma clot represents about 10-25% by weight of the starting material. Also, at any time a stabilizer may be added to the plasma to protect it during dehydration and rehydration. These stabilizers may include without limitation glycogen, sorbitol, mannitol, trehalose, maltitol, xylitol, isomaltitol, erythritol, amylase, amylopectin, inositol hexasulphate, sulphated beta-cyclodextran, etc. or combinations thereof. In fact, the stabilizer may be any known nontoxic polysaccharide according to the general formula of $C_n(H_2O)_{n-1}$ where n is between 200 and 2500. For those bioplastics in which significant retention of biological activity of constituents is desired, the plasticizing temperature is between 55-65° C. If retention of biological activity is not necessary the clotted dried plasma containing composition may be plasticized at temperatures up to about 150° C., particularly to create harder and/or denser bioplastic materials. In any case, the clotted dried plasma containing admixtures of the present invention are plasticized at 9-25 kpsi (kilopounds per square inch), preferably at 9-15 kpsi and more preferably at least 10.7 kpsi or higher. The resulting plasma-based plastics (PBPs) of the present invention can thus be made with a range of biomechanical and degradation properties. PBPs can be used in a variety of clinical applications, including their use as substitute graft materials, drug delivery carriers, anti-adhesion and barrier membranes, and scaffolds for tissue engineering. PBPs can also be used in cell culture as a non-animal source of endogenous or exogenous growth media.

One embodiment of the present invention is a method of manufacturing autologous bioplastics by processing a patient's own donated blood plasma—and products produced thereby. A typical method of making such an autologous PBP is as follows. Blood is collected prior to surgery. The blood is spun down to obtain platelet-rich plasma (PRP) and/or platelet poor plasma (PPP) and/or serum, or comparable methods such as whole blood collection or via apheresis are used to collect plasma from the patient without having to collect whole blood. The plasma is then clotted with calcium, thrombin or other known clotting agents, and the clotting when performed on platelet-rich plasma forms a platelet-rich plasma gel. To make rubbery-to-hard plastics, the platelet-rich plasma gel is first processed into a powder by drying it (this can include first removing any retained serum or not, although it is also possible to use only serum by drying it into a powder) and then ball milling or grinding or other powdering techniques. The drying step may or may not include lyophilization, but plasma dried "through the gel phase" for use in elastomers generally should not be lyophilized if possible (see below). Alternatively, a serum-free powder can be formed by first removing serum from the gel by spinning and then drying and comminuting the remaining plasma. In general, then, the present invention can use whole plasma or plasma from which one or more constituents has been removed as desired (even to the point of only serum's remaining).

Prior to further processing, the plasma powder or dried plasma gel may be treated (washed) with ethanol or propanol to sterilize it and, if desired, to remove unwanted salts from the plasma by removing the wash-step alcohol. The sterilized dried plasma can then be further composited with one or more of growth factors, drugs or other therapeutics, fillers, porogens, crosslinkers, plasticizers, and stabilizers, and then formed into a rubbery-to-hard plastic material according to methods described in PCT patent application PCT/US06/29754, incorporated herein by reference. Exogenous excipients or stabilizers including but not limited to sorbitol, mannitol and/or trehalose may be added to the plasma prior to processing to protect endogenous plasma proteins during lyophilization and/or subsequent milling. When it is necessary to minimize heat and shear damage to plasma proteins the powder formation technique may include without limitation jet milling, mechanical grinding/sieving, ball milling (as mentioned above) or other forms of particulate milling. The powder, with or without serum components, can be augmented with exogenous therapeutics (growth factors, drugs, analgesics, chemotherapeutics, antibiotics), fillers, porogens, crosslinkers and plasticizers, and then formed into rubbery to hard plastics. In addition, putty-like graft packing materials can be made by milling the plastics into pellets and mixing the pellets with self-hardening bone cements at the time of surgery.

To make elastic sheets, the clotted plasma is processed according to methods described in U.S. patent application Ser. No. 11/495,115, also incorporated herein by reference. It should be noted that platelet rich plasma has inherent antimicrobial properties, and therefore may not require exogenous factors to be added to produce an antimicrobial effect if such a property is desired. Alternatively, platelet-poor plasma is also useful in creating either autologous or allogenic plastic implants or other patient biomaterials.

As described above, the clotted and dried plasma generally retains a water content of 5-15%, more preferably 8-12%, and most preferably 8-10%. Different plasma-containing materials of the prior art have failed to create adequately cohesive polymer bases, and one reason may have been the absence of retained water to facilitate the plasticizing process.

Fabricated plastics can be milled or otherwise shaped by various approaches including but not limited to surface texturing, cutting and grinding. Surface textures can either be machined post-fabrication or can be molded into place. Alternatively, defined nano- and micro-textures can be imparted by molds used to form plastics, allowing direct molding of surface textures during bioplastic fabrication. Such textures may facilitate cell adhesion and/or physically direct cell behavior to the PBPs.

It is possible to practice the invention in an integrated system which can be, for example, installed in a blood bank. It should be noted that although an important embodiment of the present invention is the use of autologous plasma as a starting material for a patient's own bioplastic implant, pooled plasma or exogenous (allogenic) plasma may also be used to create shelf-stable implants and other materials that need not be custom manufactured patient-by-patient. In addition, the present bioplastics can be used as interfaces between tissues and prostheses to improve integration. Such a system can include a centrifuge, a dryer, a powder miller, disposable molds in standard shapes, compression molds and a cooperating hot press, and a vacuum degasser. Custom molds, based on CT/MR imaging data, could also be made by using a compact CNC milling machine, on site, or by external vendors. Compression molds made out of disposable, high compression strength materials, for example polyetheretherketone (PEEK), eliminates the need for cleaning and sterilizing standard molds between usages. Of course, the system need not be present in a blood bank or hospital.

Figure 4:
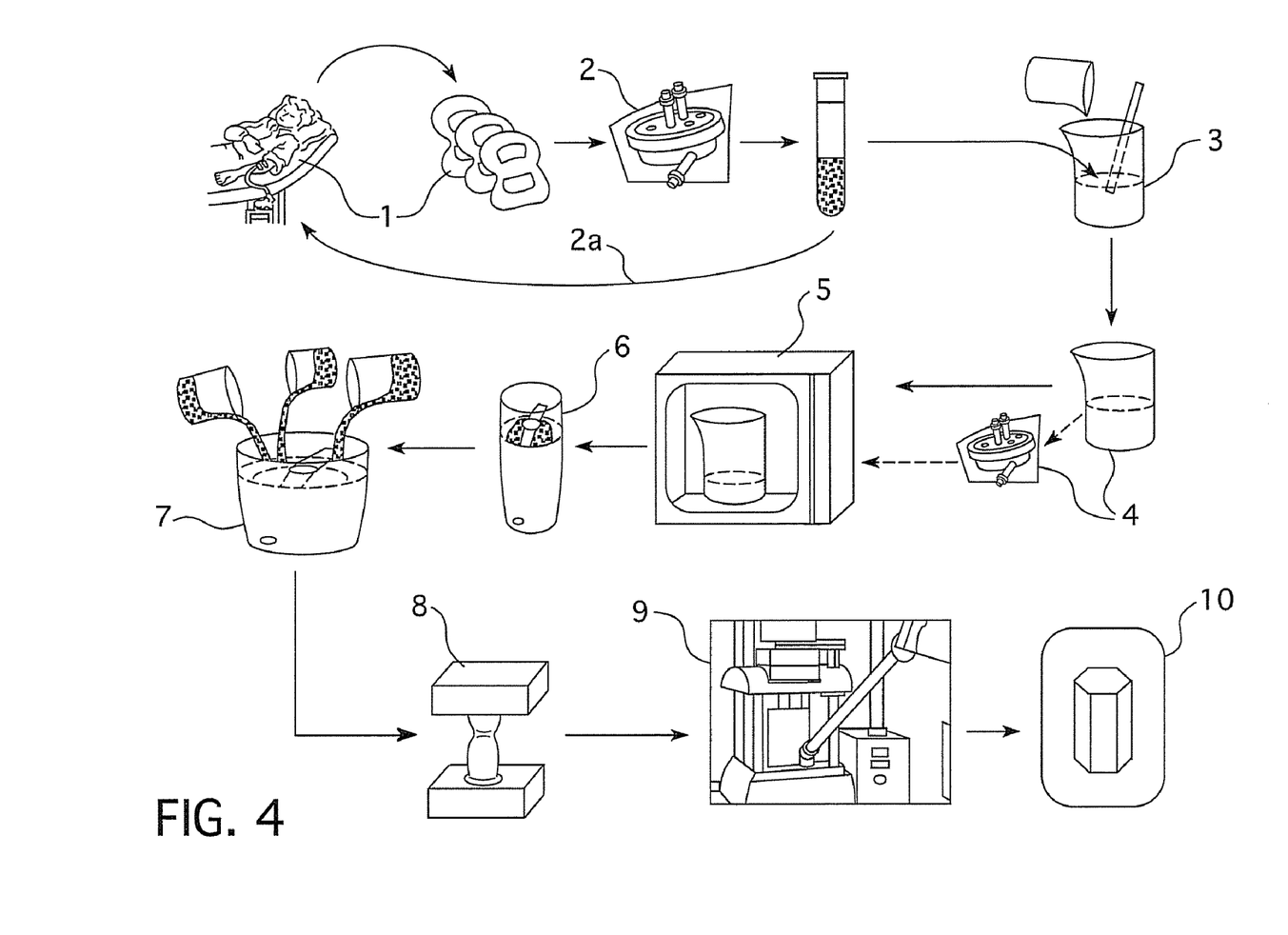
FIG. 4 is a schematic flow diagram of one embodiment of the present method for making a bioplastic from plasma.

Referring now to FIG. 4, a schematic showing one embodiment of the preparation of a rubbery-to-hard inventive bioplastic from clotted, dried and powdered plasma, a patient donates blood (1) which is spun down (2) into separated PRP or PPP plasma and red blood cells, and optionally the red blood cells are reinfused into the patient (2a). The plasma is admixed with calcium, thrombin or other clotting agent to clot the plasma (3) and to create a gel comprised of plasma clot and serum (4). The gel is dried (5) and ground into a powder or otherwise comminuted (6). (For elastomeric materials the gel is dried through the gel phase but is not powdered—not shown.) The clotted dried plasma is then blended into a dough with glycerol and/or water as a plasticizer (7), together with adding any optional ingredients, excipients, biologicals, drugs or other ingredients which do not contribute substantially to the bioplastic itself, and/or a thermoplastic polymer additive which supplements the bioplastic matrix (7). The composited dough is packed into a compression mold (8) and plasticized at controlled, usually low, temperature, and under pressure (9), to make an embodiment of the present bioplastic (10). Alternatively, the same dough can be extruded instead of molded, according to means known in the art.

Forty-five (45) L of plasma, and possibly more, may be safely harvested by apheresis from a healthy individual every year. Taking only 25 L of plasma containing 10 grams of plasma-fibrin protein/L would yield 250 grams plasma-fibrin protein/year. Stated differently, a liter of platelet rich plasma yields 100 g solids. Considering that this yield can be mixed with various extenders, such as nanoparticulate calcium phosphate and plasticizers of various types, such as 1 part plasma to 3 parts extender(s), this would yield 1 kilogram of plastic per year per human donor. Alternatively, 100 g solids plus 66 g glycerol by weight will yield 166 g bioplastic, enough to constitute 132 cubic centimeters. The powdered plasma may be stored essentially indefinitely as a lyophilized powder or as a formed plastic under the appropriate conditions. Therefore, banking of materials becomes possible for private and/or military applications. Custom molds and compression molds, and/or extrusion, as described above may be included.

In the event of the use of pooled plasma, precautions are taken against diseases including but not limited to blood-borne pathogens. The pooled or non-autologous products are useful in the event of a traumatic event or emergency in which the patient has no opportunity to stockpile blood or plasma in advance of a surgery or procedure. Blood banks and hospitals therefore might well find it advantageous to manufacture and store such plastics, or their immediate components, and therefore salvage at least a portion of blood that has been collected but is nearing the end of its shelf life. For anticipated usage of these bioplastics, blood typing is unnecessary for most allogenic applications. However, conventional blood typing procedures could be used to ensure maximum compatibility between the patient and the products made from these plastics and components.

Uses and applications of bioplastics formed with the present clotted and powdered plasma fractions include, without limitation: bone grafts, including packing materials; tissue engineered scaffolds (particularly to coordinate with a patients' own stem cells as stem cell culture becomes a commercial reality); fixation devices; surgical guides; scaffolds for tendon repair; prosthetic/tissue interfaces; sutures; nerve guides; wound protection; and protection of dura.

The method as described in association with FIG. 4 emphasizes the preparation of a dough and then the molding or extrusion of the resulting bioplastic dough. Fabrication can also be by powder molding according to the following alternative method. Molds are filled with powdered materials, including the powdered plasma, and subsequently infiltrated with plasticizer such as glycerol under positive pressure. Similarly, negative pressure may be applied to the bottom of the powder bed as glycerol, or other plasticizer, is applied over the top, or a combination of both, by vacuum casting. The resulting powdered structure can be compacted by compression molding according to PCT/US06/29754.

As an alternative to molding, powdered materials can be selectively deposited, voxel-by-voxel and layer-by-layer into a mold cavity to form either homogenous or heterogenous 3D structures. Then, glycerol, or other plasticizer, can be infused into the structure under positive pressure, or by applying a negative pressure to the bottom of the powder bed as glycerol is applied over the top, or a combination of both. The resultant powdered structure may be compacted by compression molding according to PCT/US06/29754.

Elastomeric sheets may, without limitation, include layered, rolled or tube structures and may include machined sheets which may include the processing step of punching out or otherwise forming holes, possibly of defined geometries or patterns, to facilitate host tissue interstitial communication throughout the construct. Topical applications of sheet materials include, without limitation, skin substitutes following burn and chronic non-healing wounds/sores; surgical soft tissue defect fillers; post skin and breast cancer resection; plastic surgery related applications to help minimize scarring; and dental applications, including guided tissue regeneration. Interior (rather than topical) applications include duraplasty, peripheral nerve guides, adhesion prevention in various applications such as gastrointestinal and cardiovascular surgery, hernia repair, degradable thermal insulators for cryosurgery, renal applications, anastomoses, tendon/ligament repair, heart valves and patches, bursa repair to prevent adhesions, and drug delivery of growth factors, analgesics, chemotherapeutics, antibiotics and other drugs via implanted reservoirs or impregnated plastics with or without pores.

Solid forms of the present materials (with solid ranging from rubbery plastic to very hard plastic) may be used for any of the above-mentioned applications or also in fillers or shaped grafts for craniofacial, dental, orthopaedic, neurosurgical and plastic surgical applications; or in "granular" filler, tubes and other shapes to fill defects due to trauma, cancer resection, spinal fusion, cranial defect, diseased or degraded joints such as due to arthritis or osteonecrosis; or in resorbable implants for arthroplasty, prosthetic-to-prosthetic interfaces; degradable screws, plates and other fixation devices; cartilage and meniscus graft applications; to provide fillers for cartilage defects; to create intervertebral disks to use as replacements for failed or failing disks; and to create bone resurfacing molds. Solid forms may also be used in tissue engineering applications, with capability also to deliver cells and/or growth factors for a wide range of tissue types. Such autogenic plasma-based plastic scaffolds may also be formed so as to incorporate autogenic adult stem cells. With the ever increasing banking of cord stem cells, the structures described herein could meet the demand for scaffolds capable of delivering stem cells for other than hematopoeitic stem cell applications. Microbarbs can be used for attaching graft materials, including corneal grafts, cartilage grafts, for blood vessel and other tubular structure anastomoses. Finally, for cell culture applications PBP wafers can be constructed and placed in cell culture dishes, or porous spheres can be suspended in cell culture. Armed with the disclosure herein and the inventive feature of making bioplastic from autologous or allogenic plasma or plasma fraction(s) with at least one plasticizer, the remainder of the features and characteristics of the material can be readily controlled by those skilled in the art.

Incidentally, the market potential is significant. Bone grafts, including autografts, allografts and synthetics are far from ideal, yet these are currently the second most implanted of all biomaterials (blood products are first). Autologous plastics could economically address many of the problems associated with the current options. Beyond bone grafts, there are many other important applications, such as nerve guides, prosthetics/tissue interfaces, tendon repair, and wound protection bandages. A potential business model is an integrated plastics manufacturing system for hospitals that can be placed in or adjacent existing blood banks, including (as recited above) a centrifuge, a dryer, a powder miller, disposable molds in standard shapes, compression molds and a cooperating hot press, and a vacuum degasser. Another business model is batch manufacturing in any location.

The following examples are illustrative. In general, initial experiments were performed using rabbit and human plasma testing such variables as dried plasma particle size, percent plasticizer (such as glycerol), plasma powder/plasticizer equilibration time, and processing temperature and pressure. Furthermore, ammonium acetate porogen and genipen crosslinking validation experiments have been performed. In general, as overall conclusions, when plasma powder/plasticizer ratio is 55/45 and is held constant, and mixing equilibration time for dough mixing is varied, the resulting relative hardness of the bioplastic decreases as the dough incubation time increases. However, when plasticizer concentration is varied, while holding dough mixing and processing temperature and pressure constant, such an approach results in a decrease in relative hardness of the bioplastic as the relative plasticizer concentration increases.

When making elastomeric sheet materials from the present collected, clotted and dried plasma (dried through the gel phase as to one or more plasma fractions, but not powdered), it is possible to make elastomeric sheets based on plasma from either platelet rich or platelet poor plasma clotted and dried down through the gel phase. When making elastomeric plastic sheet materials from plasma in this way, it should be noted that lyophilization may not be used as the drying method for platelet rich plasma unless one adds additional thrombin to the plasma during or after clotting of the plasma. Also, when processing plasma for use in elastomeric sheet type materials, it is useful to use existing "gel dryers" known in the art to dry the plasma through the gel phase.

As with fibrin or other protein-based plastics we have tested, plasma powder based plastics can be readily crosslinked with a crosslinker such as, without limitation, Genipin ((Methyl)1R,2R,6S)-2-hydroxy-9-(hydroxymethyl)-3-oxabicyclo[4.3.0]nona-4,8-diene-5-carboxylate). Genipin can be added as a powder up to about 2% by weight of the powder weight, prior to dough mixing and plasticizing. Preferably, Genipin powder (known in the art) is solubilized in alcohol, such as ethanol, methanol, glycerol, isopropanol, propylene glycol, or any of the di-, tri- or tetra-polyethylene glycols and is incorporated into the plasma-based bioplastic dough in the amount of about 2% Genipin by weight of the dough (net of the alcohol or polyol carrier). Interestingly, an alcohol is used to sterilize the plasma powder, Genipin or other crosslinking agent may be added to the ethanol during sterilization, and can be retained in the bioplastic dough while the alcohol fraction is removed. It should also be understood that Genipin is preferably admixed into the bioplastic dough in solution—or and it can be infused into a plasma gel in solution—but it may also be incorporated as a dry powder with any of the present bioplastic ingredients at any step of processing. Other crosslinkers, both water- and alcohol-soluble, known in the art may be substituted. By example, proanthocyanidin may be used. Similarly, the introduction of particulate ammonium acetate crystals, pre-sized to 150-250 microns, during the dough mixing phase, and following sublimation (drying under vacuum) post processing, resulted in a controlled porous plastic with a pore size of 150-250 microns. Other porogens known in the art may be substituted.

Sterilization of PBPs can be performed throughout processing, ranging from screening of plasma based on established donor collection protocols, by techniques known and developing for bacterial and viral minimization, alcohol, gamma- or other sterilization techniques of plasma powder and/or final post-packaging that represents minimal loss of biological activity, such as gamma radiation and ethylene oxide gas.

The following examples are illustrative.

EXAMPLE 1

As an example of initial biocompatibility of plasma-based plastics, plasma-based constituents (plasma powder/glycerol 55/45) were vibratomed to 300 micron thickness samples and sterilized via incubation in 70% ethanol for ten minutes. MG-63 human osteoblastic cells were seeded upon samples and incubated for three days. Cell containing samples were processed for scanning electron microscopy (SEM). Cells exhibited ready binding, proliferation and migration upon the bioplastic surface. Furthermore, cell proteolytic remodeling of the plastic was readily apparent and extensive cellular processes are interacting directly with the bioplastic, with proteolytic degradation creating a porous material from a smooth surface.

EXAMPLE 2

Rabbit plasma bioplastic samples were prepared and placed in cell free serum containing cell culture medium and held at 37° C. for up to 60 days. Samples were weighed and measured for surface area at indicated times. The bioplastic was found to swell about 50% upon addition to media but thereafter to remain constant in size throughout the duration of sampling. This indicates that the present bioplastic will not spontaneously degrade consistent with cell proteolytic degradation.

EXAMPLE 3

Human plasma powder was sized into $\leq 38$ micron and $\leq 150$ micron distributions. Using similar processing conditions to those described in the first sentence of Example 1, processed slurries were thermomechanically molded into micron peg molds. The smaller particle size of $\leq 38$ microns resulted in finer structural features compared to particle sizes of $\leq 150$. It is believed that the present particle size ranges for the human plasma powder are preferably 38-500 microns, more preferably 50-200 microns and most preferably 75-150 microns.

EXAMPLE 4

Retained biological activity in plasma based plastics (PBPs). Due to processing parameters we are able to retain biological activity within PPBs. This biological activity results primarily, but not exclusively, as a function of growth factors and extracellular matrix (ECM) molecules contributed by platelets and to a somewhat lesser extent the plasma itself. Our principle processing parameter that clearly establishes the ability to create bioplastics with substantially preserved biological activity of biological constituents is the "low" temperature processing during plastification. Historically, both US and Hungarian art was based on "high" temperature processing well above 100° C. Knowledge of tissue repair promoting growth factors and ECM molecules contained in blood was not discovered until several decades later. Furthermore sterilization was based upon steam sterilization which completely denatured any biological activity with the purified blood proteins used historically, resulting in essentially a complete denaturation of any biological components. We teach the art of low temperature processing of <65° C. when it is the purpose of the resulting plastic to retain growth factor activity. The critical temperature range is 55° C. to 65° C. with the preferred temperature being 60° C. Below 55° C. the plastification reaction can be incomplete while increasing temperature to above 65° C. results in significant loss of biological activity. However, if the purpose of the PBPs is mechanical not biological, higher temperature of up to 140° C. and even in some cases 150° C., can result in superior mechanical characteristics.

There are two important aspects to temperature, namely, magnitude and duration. Table 1 illustrates the importance of temperature duration. As pressing time at 60° C. increases from 7.5 to 30 minutes there is a significant loss in biological activity in the resulting PBPs. Biological activity was determined by taking known quantities of PBP samples, pulverizing to powder under liquid nitrogen, extracting soluble growth factors from the powder, and determining the ability of powder extracts to stimulate osteoblastic precursor cell proliferation in vitro.

TABLE 1

Effect of pressing time on biological activity of PBP

| Pressing Time[1] | Biological Activity (% above control)[2] |
|---|---|
| Serum Control[3] | 158[4] |
| PBP: 7.5 min | 285 |
| PBP: 15 min | 150 |
| PBP: 30 min | 48 |

[1]PBP pressed at 60 C. at 10.7 kspi for indicated times
[2]% above non-serum, cell culture media control
[3]10% FBS in cell culture media
[4]Values represent the mean of triplicate determinations

EXAMPLE 5

Interestingly, pressing temperature appears to have little or no impact on biological activity. An example experiment is presented in Table 2. Therefore, temperature not pressure is the limiting factor in retention of growth factor biological activity in PBPs.

TABLE 2

Effect of pressing pressure on biological activity of PBP

| Pressing Pressure[1] | Biological Activity (% above control)[2] |
|---|---|
| Serum Control[3] | 148[4] |
| PBP: 60 C., 10.7 kspi | 96 |
| PBP: 60 C., 14.7 kspi | 120 |
| PBP: 55 C., 10.4 kspi | 142 |
| PBP: 55 C., 14.7 kspi | 148 |

[1]PBP pressed at indicated temperature and pressure for 15 min
[2]% above non-serum, cell culture media control
[3]10% FBS in cell culture media
[4]Values represent the mean of triplicate determinations

EXAMPLE 6

Figure 1:
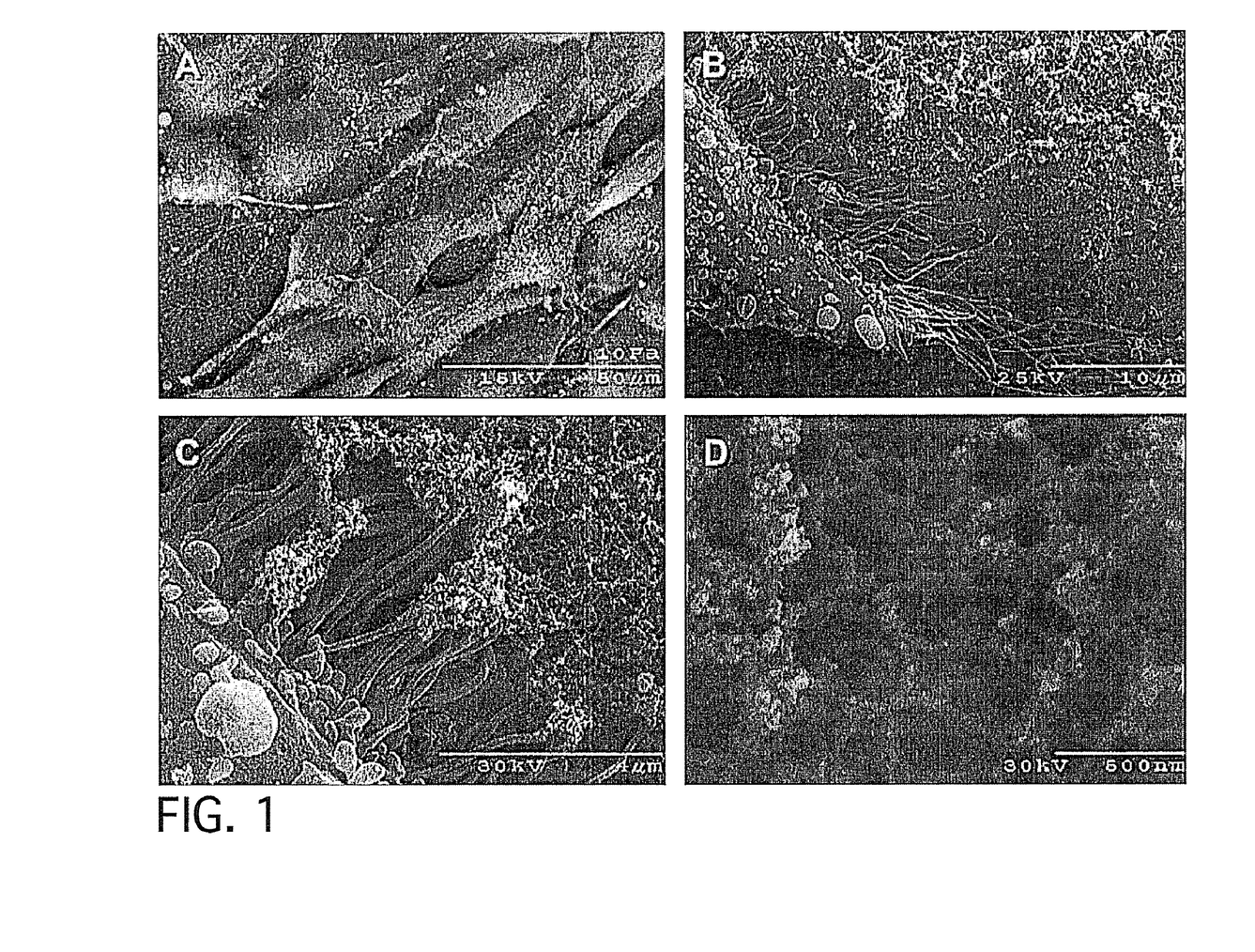
FIG. 1 are electron micrographs taken after osteoblastic precursor cells were cultured on PBPs and then monitored for subsequent cell interactions using scanning electron microscopy.

Another example of retained biological activity as well as biocompatibility is shown in FIG. 1. Osteoblastic precursor cells were cultured on PBPs and then monitored for subsequent cell interactions using scanning electron microscopy. Increasing magnification from FIG. 1A-1D illustrate positive cell-PBP interaction with active remodeling of the PBP substrate.

EXAMPLE 7

Figure 2:
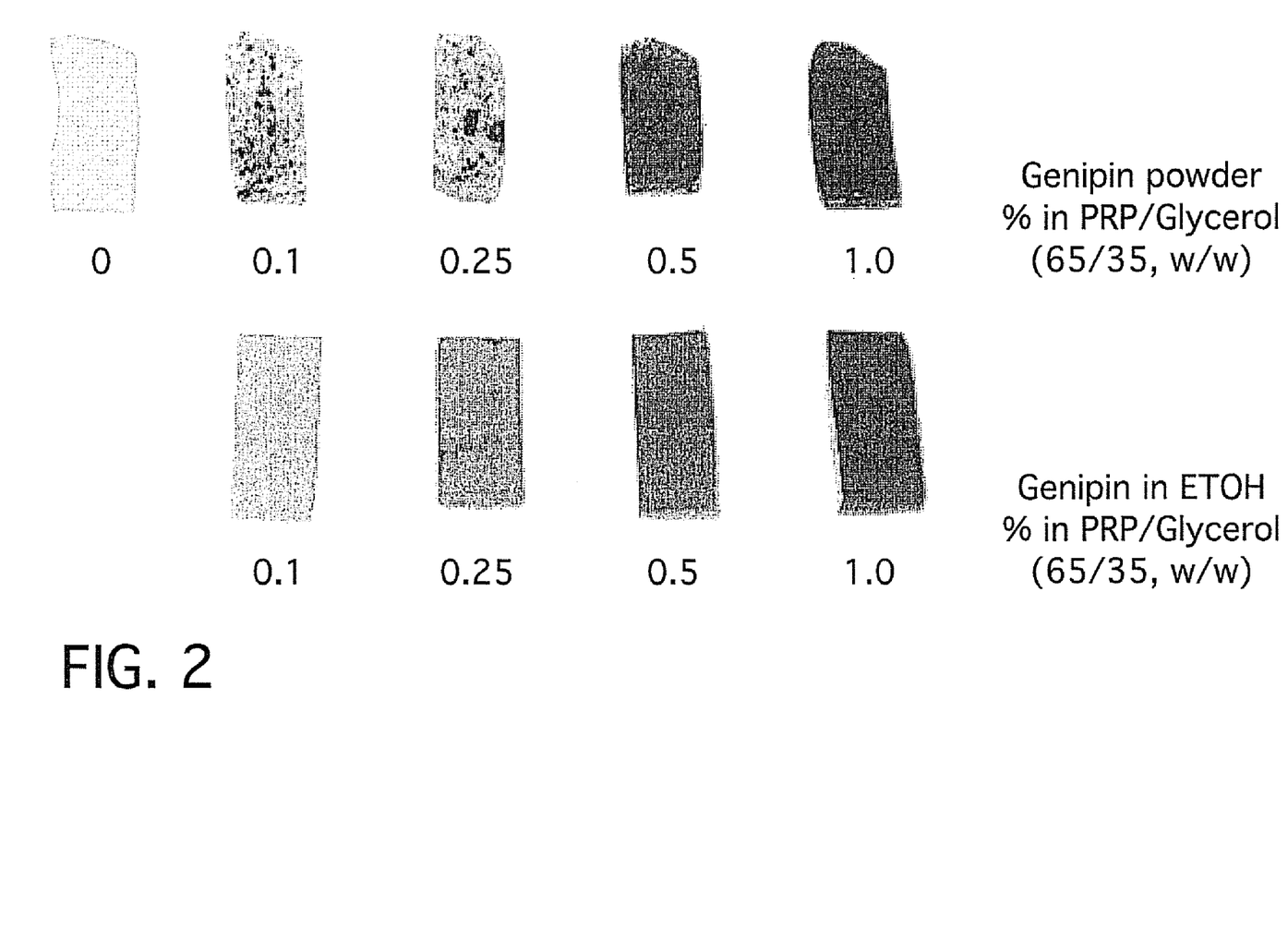
FIG. 2 is a collection of photographs showing samples of the present bioplastic in which (top row) Genipin is added as a powder to the plasma bioplastic base without prior alcohol solubilization and (second row) Genipin is added to the plasma bioplastic base after solubilization in alcohol.

Genipin modification of PBPs. Historically, prior art has either not utilized chemical crosslinking to modify protein-based biomedical plastics or has used toxic crosslinking agents such as formaldehyde. With the use of formaldehyde, purified fibrin-based plastics could be maintained in vivo for time frames approaching one year. However, formaldehyde remains a toxic substance and crosslinking procedures occurred post-plastification. Post-plastification processing is rather complex procedure requiring extensive, multiple sequences to minimize undue swelling of the plastic due to temporal differences in water transport and the formaldehyde crosslinking reaction. The present approach is to utilize Genipin, a natural plant-based chemical crosslinker 1000s of times less toxic than formaldehyde, and as we teach here the Genipin can be added prior to plastification. Because transport of Genipin is not an issue, crosslinking occurs during plastification, stabilizing the PBPs and minimizing any swelling when placed in biological fluids. In addition, we disclose here not only of the timing of the addition of the Genipin, but also the form in which it is added to the preplasticifaction dough. FIG. 2 demonstrates that desolving Genipin crystals in ethanol prior to addition to the bioplastic dough results in a more homeogenous distribution of crosslinking (the second line of bioplastic samples is demonstrably more homogeneous than the top line). Note that when Genipin is delivered in crystalline form, it first dissolves locally within the forming PBP, resulting in "islands" that eventually create a non-homogenous distribution of crosslinking in PBPs. When Genipin crystals or powder are solubilized in ethanol prior to adding to the bioplastic dough phase, a homogenous color change occurs throughout the PBPs creating a more monolithic product.

As we have shown previously, Genipin treated plastics promote residence time in biological environments. Also, within the context of delivering growth factors and other biological components, although there is a slight loss in biological activity, substantial biological activity remains in Genipin treated PBPs (Table 3). Biological assessments were conducted as with Table 1 and 2. There is no difference between the forms of Genipin added to the bioplastic dough, either crystalline or dissolved in ethanol.

TABLE 3

Effect of genipin on biological activity of PBP

| PBP Sample[1] | Biological Activity (% above control)[2] |
|---|---|
| Serum Control[3] | 286 ± 22[4] |
| PBP: No Genipin | 147 ± 2.5 |
| PBP: 2% Genipin (powder) | 105 ± 4 |
| PBP: 2% Genipin (ETOH) | 102 ± 5 |
| PBP: ETOH | 127 ± 6 |

[1]PBP pressed at 60 C., 10.7 kpsi for 15 min
[2]% above non-serum, cell culture media control
[3]10% FBS in cell culture media
[4]Values represent the mean ± SEM of triplicate determinations As expected, the inclusion of genipin in PBPs has a significant influence on PBP mechanical properties, with the inclusion of genipin increasing the Young's modulus by 4-9 fold (Table 4).

TABLE 4

Mechanical properties of PBPs

| % Genipin | Young's Modulus GPa | Max Stress MPa |
|---|---|---|
| Powder | | |
| 0 | 9 | 1.36 |
| 1 | 50 | 1.16 |
| 2 | 80 | 2.19 |
| Powder + Water | | |
| 0 | 9 | 0.8 |
| 1 | 40 | 1.2 |
| 2 | 60 | 1.1 |
| ETOH | | |
| 2 | 40 | 2.4 |

PBP were 65/35 PRP/glycerol (w/w) pressed at 60 C., 10.7 kpsi for 15 min

EXAMPLE 8

Figure 3:
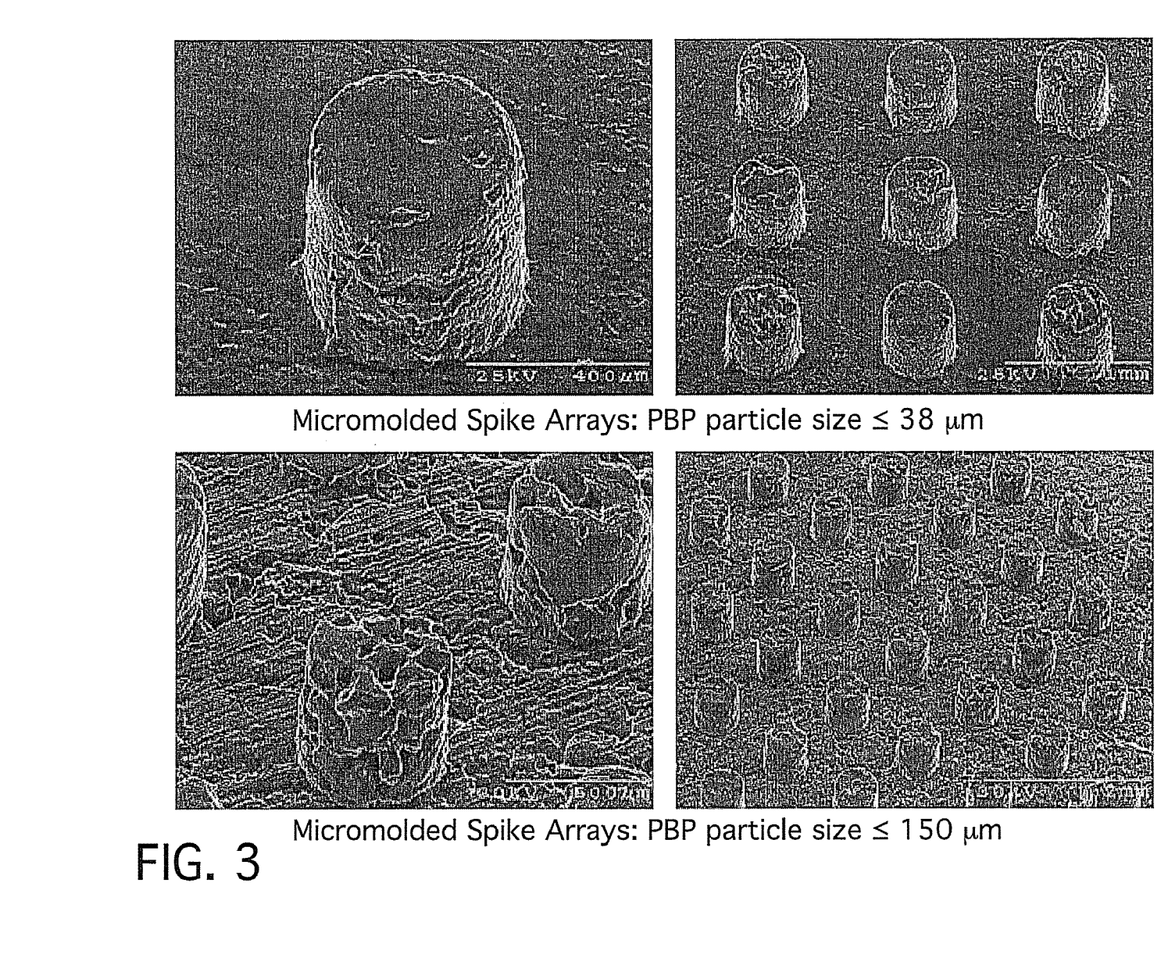
FIG. 3 is a set of micrographs that illustrate how smaller particle sizes enable more and better uniformity in mold fill and molded product.

Lyophilized plasma particle size on PBP characteristics. Another aspect to PBP formulation where we teach new art is particle size of source biological powder for bioplastic dough preparation. Historically, purified protein starting materials were screened to remove large particles, but there is nothing in the prior art concerning the importance of initial powder particle size and the resulting PBP characteristics. As the particle size becomes smaller this denotes a faster equilibration time of "wetting" powder with added plasticizer during the dough preparation. Smaller particle size enables more uniform mold fill as demonstrated in FIG. 3. These properties are desirable during micromolding or for micromachining preparation of PBP; whereas, larger particle size will enable better macromolecular interlock between particles during plastification, resulting in PBPs with greater mechanical properties.

EXAMPLE 9

Addition of calcium phosphate particulates to PBPs. Calcium phosphate particulates can be added during PBP dough preparation to create PBP with both organic and inorganic components. FIG. 4 shows the addition of up to 10% nano-particulate tricalcium phosphate (TCP) powder during dough formation with an increase in PBP opacity as TCP concentration increases. Alternatively, other clinically relevant forms of calcium phosphate, including but not limited to hydroxyapatite, can be substituted or mixed with TCP. The inclusion of such materials will alter mechanical properties, degradation, growth factor release rates, and provide additional osteoconductivity.

EXAMPLE 10

Uncrosslinked PRP-PBP is stable under in vitro conditions. PRP based PBP was placed under simulated in vivo conditions, 37° C. in serum containing media for 60 days. A slight swelling occurred within the first day, but there was no subsequent change throughout the incubation period.

Although the invention has been described with particularity above, with reference to specific materials and methods and results, the invention is only to be claimed insofar as is set forth in the accompanying claims.

The invention claimed is:

1. A method for making a plasma based plastic comprising: a) collecting a quantity of plasma, wherein said plasma is separated from whole blood; b) clotting said plasma; c) drying said clotted plasma, wherein said drying comprises lyophilization; d) contacting a quantity of the clotted dried plasma with at least one plasticizer to make a dough; and e) shaping and heating said dough to make a bioplastic article.

2. The method according to claim 1, wherein at least one plasticizer is added to said quantity of plasma either before or after the step of clotting said plasma.

3. The method according to claim 1, wherein a crosslinking agent is added to said quantity of plasma either before or after the step of clotting said plasma.

4. The method according to claim 1, wherein said quantity of plasma is a pooled quantity of plasma from a plurality of mammalian donors and wherein a crosslinking agent is added to said quantity of plasma either before or after the step of clotting said plasma.

5. The method according to claim 1, wherein said quantity of plasma is a pooled quantity of plasma from a plurality of human donors.

6. The method according to claim 1, wherein said quantity of plasma is collected from a single human donor.

7. A method for making a plasma based plastic comprising: a) collecting a quantity of human plasma, wherein said plasma is separated from whole blood; b) clotting said plasma; c) drying said clotted plasma, wherein said drying comprises lyophilization; d) contacting a quantity of the clotted dried plasma with at least one plasticizer to make a dough; and e) shaping and heating said dough to make a bioplastic article.

8. The method according to claim 1 or 7, wherein said dough is heated at a temperature between 55-65° C.

9. The method according to claim 1 or 7, wherein said dough is heated at a temperature of no higher than 150° C.

10. The method according to claim 1 or 7, wherein the dough is shaped and heated at a pressure between 9-25 kilopounds per square inch.

11. The method according to claim 1 or 7, wherein the dough is shaped and heated at a pressure of at least 10.7 kilopounds per square inch or higher.

12. The method according to claim 1 or 7, wherein a porogen compound is added to the dough prior to shaping and heating.

13. The method according to claim 1 or 7, wherein said plasma is collected via apheresis.

14. The method according claim 1 or 7, wherein said plasma is whole plasma.

15. The method according to claim 1 or 7, wherein said plasma is platelet-rich plasma or platelet-poor plasma.

16. The method according to claim 1 or 7, wherein said plasma is plasma from which one or more constitutents has been removed.

17. The method according to claim 1 or 7 wherein the at least one plasticizer is selected from the group consisting of glycerol and water.

18. The method according to claim 1 or 7 wherein a stabilizer is added to said quantity of plasma and wherein said stabilizer is selected from the group consisting of glycogen, sorbitol, mannitol, trehalose, maltitol, xylitol, isomaltitol, erythritol, amylase, amylopectin, inositol hexasulphate, sulphated beta-cyclodextran, and combinations thereof.

19. The method according to claim 1 or 7 wherein the dough is crosslinked by adding genipin as a powder to the clotted dried plasma in the amount of about 2% by weight of the dried plasma.

20. The method according to claim 19 wherein said genipin is solubilized in alcohol before adding said genipin to the dough.

21. The method according to claim 1 or 7 wherein the clotted dried plasma is adjusted to a percentage water by weight of 5-15%.

22. The method according to claim 1 or 7 wherein ammonium acetate is added to the dough prior to shaping and heating.

23. The method according to claim 1 or 7 wherein prior to shaping and heating, the dough is combined with a quantity of particulate ammonium acetate crystals, pre-sized to 150-250 microns, and wherein during the shaping and heating the ammonium acetate crystals sublimate to result in a controlled porous plastic with a pore size of 150-250 microns.

24. The method according to claim 1 or 7 wherein said quantity of plasma is clotted, dried and comminuted to a particle size distribution of between 38-500 microns.

25. The method according to claim 1 or 7 wherein the dough is heated at a temperature between 100-140° C.

26. The method according to claim 1 or 7 wherein prior to shaping and heating, up to 10% nanoparticulate tricalcium phosphate is added to the dough.

* * * * *

UNITED STATES PATENT AND TRADEMARK OFFICE
CERTIFICATE OF CORRECTION

| | |
|---|---|
| PATENT NO. | : 8,293,530 B2 |
| APPLICATION NO. | : 11/873751 |
| DATED | : October 23, 2012 |
| INVENTOR(S) | : Burgess et al. |

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 965 days.

Signed and Sealed this
Eleventh Day of November, 2014

Michelle K. Lee
*Deputy Director of the United States Patent and Trademark Office*